United States Patent
Yamashita et al.

(10) Patent No.: US 6,495,592 B1
(45) Date of Patent: Dec. 17, 2002

(54) TRACHEAL SMOOTH MUSCLE RELAXANTS

(75) Inventors: Shinya Yamashita, Tokyo (JP); Jiro Takeo, Tokyo (JP); Shuji Jinno, Tokyo (JP); Yasuyo Kogure, Tokyo (JP); Hiroyuki Onuki, Tokyo (JP); Takaaki Okita, Tokyo (JP); Junichiro Hata, Tokyo (JP); Yasuhiro Fukuda, Tokyo (JP); Naomi Ohtsuka, Tokyo (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 09/609,310

(22) Filed: Jun. 30, 2000

Related U.S. Application Data

(62) Division of application No. 09/101,842, filed as application No. PCT/JP97/00105 on Jan. 20, 1997, now Pat. No. 6,180,659.

(30) Foreign Application Priority Data

Jan. 19, 1996 (JP) .................................. 007904

(51) Int. Cl.$^7$ ............................................ A61K 31/335
(52) U.S. Cl. ...................................... 514/450; 514/826
(58) Field of Search .......................................... 514/450

(56) References Cited

U.S. PATENT DOCUMENTS

| 4,104,280 A | 8/1978 | Ackrell |
| 5,734,067 A | 3/1998 | Jinno et al. |

FOREIGN PATENT DOCUMENTS

| DE | 1 302 590 | 11/1970 |
| DE | 32 03 065 | 8/1983 |
| EP | 0 003 893 | 9/1979 |
| EP | 0 011 067 | 5/1980 |
| EP | 0 805 155 | 11/1997 |
| GB | 2 016 466 | 9/1979 |
| WO | 96/25927 | 8/1996 |

OTHER PUBLICATIONS

CA126:157408, Ohtani et al, WO97/00853, abstract, Jan. 9, 1997.*
Chemical Abstracts, vol. 67, No. 11, Abstract No. 54314g (1967) (XP002045041).
M. de la Fuente et al., *J. Org. Chem.*, 61(17), 5818–5822 (1996).
A. Anjaneyulu et al., *Tetrahedron.*, 40(21), 4245–4252 (1984).
T. Qian et al., *Phytochemistry*, 31(3), 1068–1070 (1992).
I. Ueda et al., *Chem. Pharm. Bull.*, 26(10), 3058–3070 (1978).
I. Ueda et al., *Chem. Pharm. Bull.*, 23(10), 2223–2231 (1975).
K. Šindelář et al., *Collection Czechoslov. Chem. Commun.*, 43, 471–497 (1977).
P. Burden et al., *J. Chem. Soc. Perkin Trans. 1*, 3291–33294 (1991).
D. Acton et al., *J. Med. Chem.*, 26(8), 1131–1137 (1983).
Carrier et al., *Br. J. Pharmac.*, 82(2), 389–395 (1984).
Kisiku et al., *Nippon Yakurigaku Zasshi*, 64(5), 299–307 (1989).
Protiva et al., CA115:49435, CS 268630 (1990).
Smrz et al., CA 93:150129, CS 179268 (1979).
Takeo et al., CA 125:275677 (1996).
Jinno et al., CA 125:86518 (1996).

* cited by examiner

*Primary Examiner*—Rebecca Cook
(74) *Attorney, Agent, or Firm*—Wenderoth, Lind & Ponack, L.L.P.

(57) ABSTRACT

The present invention offers a tracheal smooth muscle relaxant containing the compound represented by the following formula (1) or pharmacologically acceptable salt thereof as an effective ingredient.

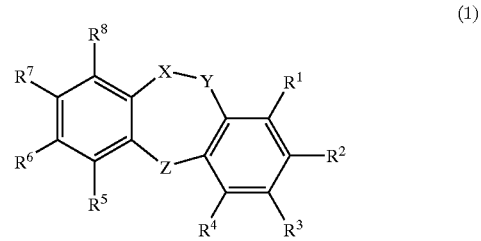

(1)

6 Claims, No Drawings

TRACHEAL SMOOTH MUSCLE RELAXANTS

This is a divisional of Ser. No. 09/101,842, filed Aug. 31, 1998 now U.S. Pat. No. 6,180,659 which is a 371 of PCT/JP97/00105, filed Jan. 20, 1997.

TECHNICAL FIELD

The present invention relates to a tracheal smooth muscle relaxant in which a derivative of dibenz[b,f]oxepin or dibenzo[b,f]thiepin derivatives is an effective ingredient.

BACKGROUND ART

Xanthine derivatives such as theophylline and $\beta_2$ agents such as salbutamol have been known as drugs having a relaxing action to tracheal smooth muscles.

However, in those drugs which have been already known, their relaxing action of tracheal smooth muscles in airway diseases and pulmonary diseases such as bronchial asthma, acute and chronic bronchitis, pulmonary emphysema and upper esophagitis is not satisfactory in terms of a balance with the side effect.

In view of the above, an object of the present invention is to offer drugs having novel relaxing action to tracheal smooth muscle exhibiting far better action to airway diseases, etc.

DISCLOSURE OF THE INVENTION

In order to solve the above problems, the present invention offers a tracheal smooth muscle relaxant containing the compound represented by the following formula (1) or pharmacologically acceptable salt thereof as an effective ingredient.

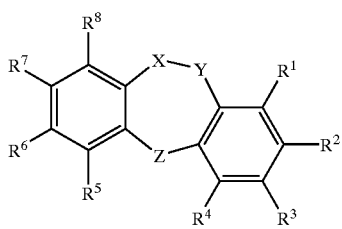

(1)

[In the formula, X and Y each is any group selected from a group consisting of $CH_2$, $CHW^1$ (where $W^1$ is halogen atom, hydroxyl group or lower alkoxy group) and C=O when the bond of X and Y is a single bond, while when it is a double bond, X and Y each is any group selected from a group consisting of CH and $COW^2$ (where $W^2$ is lower alkyl group or lower alkylcarbonyl group); Z is O, S, S=O or $SO_2$; and $R^1 \sim R^8$ each is selected from a group consisting of hydrogen atom, $VR^9$ (where V is O, S, S=O or $SO_2$; and $R^9$ is hydrogen atom, lower alkyl group, hydroxy lower alkyl group, lower acyl group, trihalomethyl group or carboxyl lower alkyl group), carboxyl lower alkyl group, hydroxy lower alkyl group, hydroxy lower alkenyl group, hydroxy lower alkynyl group, halogen atom, lower alkyl group, lower alkyl ketone, trihalomethyl group, trimethylsilylethynyl, nitro group, amino group, N-carbonyl lower alkyl group, lower alkylphenyl group and phenyl group].

BEST MODES FOR CONDUCTING THE INVENTION

As mentioned above, the present invention offers a tracheal muscle relaxant containing the dibenz[b,f]oxepin and dibenzo[b,f]thiepin derivatives represented by the above formula (1) or salt thereof as an effective ingredient and, in the formula (1), "lower alkyl" for $R^1 \sim R^8$ and $R^9$ means straight chain, branched chain or cyclic alkyl chain having up to eight carbon atoms while the pharmacologically (pharmaceutically) acceptable salt means sodium salt, potassium salt, calcium salt, ammonium salt, aluminum salt, etc.

The compound represented by the formula (1) has an excellent relaxant action to tracheal smooth muscle and has low toxicity and, therefore, it can be effectively used for airway diseases such as bronchia asthma and bronchitis, diseases accompanied by reversible obstruction of airway, asthma, acute and chronic bronchitis, chronic obstructive pulmonary diseases such as pulmonary emphysema, etc.

Incidentally, the above-mentioned compound and salt thereof can be manufactured by various chemical synthetic means and can be made into various dosage forms by conventional techniques in pharmaceutical preparations including oral preparations such as diluted powder, granules, tablets, coated tablets, ampoules and capsules; subcutaneous, intramuscular or intravenous injections; suppositories; etc. In the manufacture of those preparations, various additives such as commonly used diluents, binders, disintegrating agents, pH adjusting agents and solubilizers may be appropriately used. Dose of the above-mentioned compound of the present invention or salt thereof to a patient to be treated may vary depending upon age, type and symptom of disease, etc. of the patient but, usually, 1~5,000 mg/day may be administered to an adult once to several times daily.

As hereunder, methods for the manufacture of the dibenz[b,f]oxepin and dibenzo[b,f]thiepin derivatives which are effective ingredients for tracheal smooth muscle relaxants in accordance with the present invention, the result of the test of those compounds on tracheal smooth muscle relaxation, etc. will be exemplified whereby the embodiments of the present invention will be illustrated in more detail.

It goes without saying that the present invention is never limited by the following exemplifications.

PRODUCTION EXAMPLE 1

Production of 6,9-dihydroxy-7-methoxy-10,11-dihydrodibenz[b,f]oxepin-10-one (Compound 1)

Step 1

5-Bromovaniline (25 g) was suspended in anhydrous methylene chloride (700 ml), followed by addition of m-chloroperbenzoic acid (32 g; purity of 70%), and the resulting mixture was heated under stirring at 50° C. for 16 hours. After evaporating the solvent under reduced pressure, the residue was dissolved in ethyl acetate (700 ml), followed by washing in an aqueous saturated sodium hydrogen carbonate solution and in water, and further in an aqueous saturated sodium chloride solution, and drying over anhydrous magnesium sulfate to distill off the solvents under reduced pressure. To the resulting residue were added dioxane (76 ml) and an aqueous 3N sodium hydroxide solution (76 ml), followed by stirring at room temperature for 30 minutes. The resulting mixture was adjusted to acidity with dilute hydrochloric acid, followed by extraction in ethyl acetate three times. Washing the organic phase in water and continuously in an aqueous saturated sodium chloride solution and drying the organic phase over anhydrous magnesium sulfate to distill off the solvents under reduced pressure, the resulting residue was purified by silica gel column chromatography (developing solvent:hexane:ethyl acetate=1:1), to recover 2-bromo-6-methoxy-1,4- hydroquinone (15 g; yield of 63%). By $^1$H-NMR (90 MHz, CDCl$_3$), the compound has the peaks shown below.

δ(ppm)
3.87(3H, s, OC$\underline{H}_3$)
4.61(1H, s, O$\underline{H}$)
5.48(1H, s, O$\underline{H}$)
6.41(1H, d, J=2.8 Hz, Ar—$\underline{H}$)
6.58(1H, d, J=2.8 Hz, Ar—$\underline{H}$)

Step 2

2-Bromo-6-methoxy-1,4-hydroquinone (15 g) produced in the step 1 was dissolved in acetonitrile (400 ml), followed by addition of ammonium cerium (IV) nitrate (56.4 g) and stirring at room temperature for 20 minutes. After distilling off the solvent under reduced pressure, water and ethyl acetate were added to the residue for distribution. The ethyl acetate phase was washed in water and then in an aqueous saturated sodium chloride solution and dried over anhydrous magnesium sulfate, and after distilling off the solvents under reduced pressure, 2-bromo-6-methoxy-1,4-benzoquinone (14.7 g; yield of 99%) was recovered. By $^1$H-NMR (90 MHz, CDCl$_3$), the compound has the peaks shown below.

δ(ppm)
3.86(3H, s, OC$\underline{H}_3$)
5.96(1H, d, J=2.3 Hz, Ar—$\underline{H}$)
7.21(1H, d, J=2.3 Hz, Ar—$\underline{H}$)

Step 3

To distilled 2-allylphenol (8.4 ml) were added N,N-dimethylformamide (240 ml) and cesium carbonate (42 g), followed by further dropwise addition of 2-bromo-6-methoxy-1,4-benzoquinone (9.3 g) produced in the step 2, which was preliminarily dissolved in N,N-dimethylformamide (180 ml), and the resulting mixture was stirred at room temperature for 30 minutes. The reaction solution was diluted with ethyl acetate, washed in water and subsequently in an aqueous saturated sodium chloride solution, and dried over anhydrous magnesium sulfate, to distill off the solvents under reduced pressure. The resulting residue was purified by silica gel column chromatography (developing solvent:hexane:ethyl acetate=1:1), to recover 2-(2-allylphenoxy)-6-methoxy-1,4-benzoquinone (8.4 g; yield of 68%). By $^1$H-NMR (90 MHz, CDCl$_3$), the compound has the peaks shown below.

δ(ppm)
3.29(2H, d, J=6.6 Hz, Ar—C$\underline{H}$)
3.86(3H, s, OC$\underline{H}_3$)
4.9–5.2(2H, m, —CH=C$\underline{H}_2$)
5.55(1H, d, J=2.1 Hz, Ar—$\underline{H}$)
5.8–6.1(1H, m, —C$\underline{H}$=CH$_2$)
5.81(1H, d, J=2.1 Hz, Ar—$\underline{H}$)
6.9–7.3(4H, m, Ar—$\underline{H}$)

Step 4

2-(2-Allylphenoxy)-6-methoxy-1,4-benzoquinone (8.4 g) produced in the step 3 was dissolved in ethanol (200 ml), followed by addition of ascorbic acid (30 g) preliminarily dissolved in water (100 ml), and the resulting mixture was stirred at room temperature until the color was eliminated. After distilling off the solvents under reduced pressure, ethyl acetate extraction, washing of the organic phase in water and subsequently in an aqueous saturated sodium chloride solution, drying of the organic phase over anhydrous magnesium sulfate and subsequent distillation of the solvents under reduced pressure yielded 2-(2-allylphenoxy)6-methoxy-1,4-hydroquinone (8.5 g; yield of 100%). By $^1$H-NMR (90 MHz, CDCl$_3$), the compound has the peaks shown below.

δ(ppm)
3.44(2H, d, J=6.6 Hz, Ar—C$\underline{H}_2$)
3.88(3H, s, OC$\underline{H}_3$)
4.60(1H, s, O$\underline{H}$)
4.9–5.2(2H, m, —CH=C$\underline{H}_2$)
5.16(1H, s, O$\underline{H}$)
5.8–6.1(1H, m, —C$\underline{H}$=CH$_2$)
5.93(1H, d, J=2.8 Hz, Ar—$\underline{H}$)
6.24(1H, d, J=2.8 Hz, Ar—$\underline{H}$)
6.9–7.3(4H, m, Ar—$\underline{H}$)

Step 5

To 2-(2 allylphenoxy)6-methoxy-1,4-hydroquinone (8.5 g) produced in the step 4 were added pyridine (50 ml) and acetic anhydride (20 ml), for subsequent stirring at room temperature for one hour, prior to dilution with ethyl acetate, and the resulting solution was washed in dilute hydrochloric acid and in water, and subsequently in an aqueous saturated sodium chloride solution and dried over anhydrous magnesium sulfate. Then, the solvents were distilled off under reduced pressure. The resulting residue was purified by silica gel column chromatography (developing solvent:hexane:ethyl acetate=2:1), to recover 2-(2-allylphenoxy)-1,4-diacetoxy-6-methoxybenzene (10.6 g; yield of 96%). By $^1$H-NMR (90 MHz, CDCl$_3$), the compound has the peaks shown below.

δ(ppm)
2.23(3H, s, COC$\underline{H}_3$)
2.23(3H, s, COC$\underline{H}_3$)
3.36(2H, d, J=6.6 Hz, Ar—C$\underline{H}_2$)
3.82(3H, s, OC$\underline{H}_3$)
4.9–5.2(2H, m, —CH=C$\underline{H}_2$)
5.8–6.1(1H, m, —C$\underline{H}$=C$\underline{H}_2$)
6.14(1H, d, J=2.4 Hz, Ar—$\underline{H}$)
6.45(1H, d, J=2.4 Hz, Ar—$\underline{H}$)
6.9–7.3(4H, m, Ar—$\underline{H}$)

Step 6

2-(2-Allylphenoxy)-1,4-diacetoxy-6-methoxybenzene (10.6 g) produced in the step 5 was dissolved in methylene chloride (175 ml), methanol (175 ml) and acetic acid (20 ml), prior to stirring at −78° C. for 20 minutes. After bubbling ozone gas into the resulting solution under stirring for 3 hours, it was confirmed that the solution turned blue. Subsequently, dimethyl sulfide (11 ml) was added to the solution, followed by stirring until the temperature of the solution elevated to room temperature. After distilling off the solvents under reduced pressure, the residue was purified by silica gel column chromatography (developing solvent:hexane:ethyl acetate=2:3), to yield 2-(2,5-diacetoxy-3-methoxyphenoxy)benzyl aldehyde (8.6 g; yield of 80%). By $^1$H-NMR (90 MHz, CDCl$_3$), the compound has the peaks shown below.

δ(ppm)
2.23(3H, s, COC$\underline{H}_3$)
2.23(3H, s, COC$\underline{H}_3$)
3.74(2H, d, J=1.5 Hz, Ar—C$\underline{H}_2$)
3.84(3H, s, OC$\underline{H}_3$)
6.21(1H, d, J=2.4 Hz, Ar—$\underline{H}$)
6.51(1H, d, J=2.4 Hz, Ar—$\underline{H}$)
6.9–7.3(4H, m, Ar—$\underline{H}$)
9.72(1H, t, J=1.5 Hz, C$\underline{H}$O)

Step 7

2-(2,5-Diacetoxy-3-methoxyphenoxyl)benzyl aldehyde (8.6 g) produced in the step 6 was dissolved in a mixture solvent (484 ml) comprising tertiary butanol and 2-methyl-2-butene (4:1), followed by addition of sodium hypochlorite (8.2 g) and sodium dihydrogen phosphate (8.2 g), both dissolved in water (156 ml), prior to stirring at room temperature for one hour. The reaction solution was partitioned with ethyl acetate and water, and the resulting organic phase was washed in water and in an aqueous saturated sodium chloride solution and dried over anhydrous magnesium sulfate, and then, the solvents were distilled off under reduced pressure. To the residue was added methane sulfonic acid (120 ml), followed by stirring at room temperature for 7 days, and the resulting solution was then diluted with ethyl acetate, washed in water and in an aquoeous saturated sodium chloride solution, and dried over anhydrous magnesium sulfate to distill off the solvents. The resulting residue was purified by silica gel column chromatography (developing solvent:hexane:ethyl acetate=2:3) and recrystallized in hexane and ethyl acetate, to recover 6,9-dihydroxy-7-methoxy-10,11-dihydrodibenz[b,f]oxepin-10-one (Compound 1) represented by the following formula in yellow needles (4.6 g; yield of 70%).

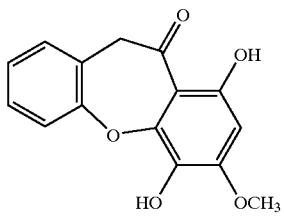

Compound 1

The compound 1 has a melting point of 220.5 to 222.0° C. By $^1$H-NMR (90 MHz, CDCl$_3$), the compound 1 has the peaks shown below.

δ(ppm)

3.94(3H, s, OC$\underline{H}_3$)

4.11(2H, s, Ar—C$\underline{H}_3$)

5.49(1H, s, O$\underline{H}$)

6.28(1H, s, Ar—$\underline{H}$)

7.2–7.5(4H, m, Ar—$\underline{H}$)

12.67(1H, s, O$\underline{H}$)

PRODUCTION EXAMPLE 2

Production of 6,7,9-trihydroxy-10,11-dihydrodibenz [b,f]oxepin-10-one (Compound 2)

0.39 g of the Compound 1 produced in Example 1was placed in a pressure-resistant reaction vessel, followed by addition of pyridine hydrochloride salt (4 g), and stirring at 200° C. for 1.5 hours. The resulting solution was partitioned between ethyl acetate and water, and the organic phase was washed in dilute hydrochloric acid, in water and in an aqueous saturated sodium chloride solution, and dried over anhydrous magnesium sulfate to distill off the solvents under reduced pressure. The resulting residue was purified by silica gel column chromatography (developing solvent:ether) and recrystallized in hexane and ethyl acetate, to recover 6,7,9-trihydroxy-10,11-dihydrodibenz[b,f] oxepin-10-one (Compound 2) represented by the following formula in brown plates (285 mg; yield of 77%).

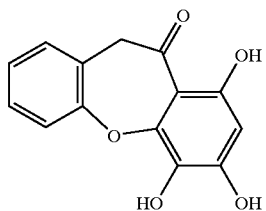

Compound 2

The compound 2 has a melting point of 224.5 to 226.5° C. By $^1$H-NMR (90 MHz, DMSO-d$_6$), the Compound 2 has the peaks shown below.

δ(ppm)

4.10(2H, s, Ar—C$\underline{H}_2$)

6.11(1H, s, Ar—$\underline{H}$)

7.1–7.6(4H, m, Ar—$\underline{H}$)

12.62(1H, s, O$\underline{H}$)

PRODUCTION EXAMPLE 3

Production of 6,9-dihydroxy-7-methoxy-4-methyl-10,11-dihydrodibenz[b,f]oxepin-10-one (Compound 3)

The same procedures as in the steps 1 to 7 of Example 1 were carried out except for the use of 2-allyl-6-methylphenol in place of 2-allylphenol in the step 3 of Example 1, to recover 6,9-dihydroxy-7-methoxy-4-methyl-10,11-dihydrodibenz[b,f]oxepin-10-one (Compound 3) represented by the following formula in pale yellow needles.

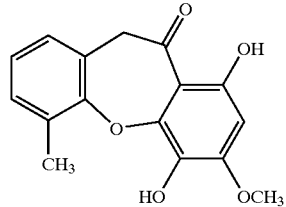

Compound 3

The Compound 3 has a melting point of 239.7 to 241.5° C. By $^1$H-NMR (90 MHz, CDCl$_3$) the Compound 3 has the peaks shown below.

δ(ppm)

2.44(3H, s, C$\underline{H}_3$)

3.88(3H, s, OC$\underline{H}_3$)

4.08(2H, s, Ar—C$\underline{H}_2$)

6.38(1H, s, Ar—$\underline{H}$)

7.0–7.3(3H, m, Ar—$\underline{H}$)

8.69(1H, brs,O$\underline{H}$)

12.72(1H, s, O$\underline{H}$)

PRODUCTION EXAMPLE 4

Production of 4-methyl-6,7,9-trihydroxy-10,11-dihydrodibenz[b,f]oxepin-10-one (Compound 4)

The same procedures as in the steps 1 to 7 of Example 1 and in Example 2 were carried out except for the use of 2-allyl-6-methylphenol in place of 2-allylphenol in the step 3 of Example 1, to recover 4-methyl-6,7,9-trihydroxy-10, 11-dihydrodibenz[b,f]oxepin-10-one (Compound 4) represented by the following formula in mud yellow plates.

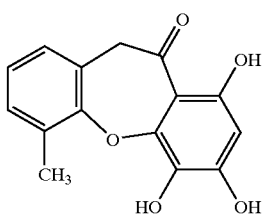

Compound 4

The Compound 4 has a melting point of 259.6 to 260.8° C. By $^1$H-NMR (90 MHz, DMSO-d$_6$), the Compound 4 has the peaks shown below.

δ(ppm)
2.46(3H, s, C$\underline{H_3}$)
4.06(2H, s, Ar—C$\underline{H_2}$)
6.16(1H, s, Ar—$\underline{H}$)
7.0–7.3(3H, m, Ar—$\underline{H}$)
12.65(1H, s, O$\underline{H}$)

PRODUCTION EXAMPLE 5

Production of 6,9-dihydroxy-4,7-dimethoxy-10,11-dihydrodibenz[b,f]oxepin-10-one (Compound 5)

The same procedures as in the steps 1 to 7 of Example 1 were carried out except for the use of 2-allyl-6-methoxyphenol in place of 2-allylphenol in the step 3 of Example 1, to recover 6,9-dihydroxy-4,7-dimethoxy-10,11-dihydrodibenz[b,f]oxepin-10-one (Compound 5) represented by the following formula in yellow needles.

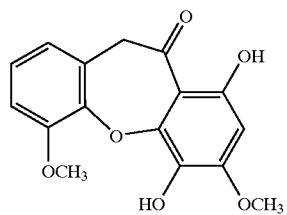

Compound 5

The Compound 5 has a melting point of 227.8 to 229.8° C. By $^1$H-NMR (90 MHz, CDCl$_3$), the Compound 5 has the peaks shown below.

δ(ppm)
3.92(3H, s, OC$\underline{H_3}$)
3.95(3H, s, OC$\underline{H_3}$)
4.14(2H, s, Ar—C$\underline{H_2}$)
6.28(1H, s, Ar—$\underline{H}$)
6.8–7.2(3H, m, Ar—$\underline{H}$)
12.59(1H, s, O$\underline{H}$)

PRODUCTION EXAMPLE 6

Production of 4,6,7,9-tetrahydroxy-10,11-dihydrodibenz[b,f]oxepin-10-one (Compound 6)

The same procedures as in the steps 1 to 7 of Example 1 and in Example 2 were carried out except for the use of 2-allyl-6-methoxyphenol in place of 2-allylphenol in the step 3 of Example 1, to recover 4,6,7,9-tetrahydroxy-10,11-dihydrodibenz[b,f]oxepin-10-one (Compound 6) represented by the following formula in mud yellow amorphous powder.

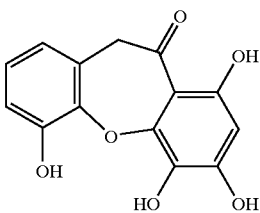

Compound 6

The Compound 6 has a melting point of 235.4 to 236.7° C. By $^1$H-NMR (90 MHz, DMSO-d$_6$), the Compound 6 has the peaks shown below.

δ(ppm)
4.10(2H, s, Ar—C$\underline{H_2}$)
6.16(1H, s, Ar—$\underline{H}$)
6.8–7.1(3H, m, Ar—$\underline{H}$)
12.54(1H, s, O$\underline{H}$)

PRODUCTION EXAMPLE 7

Production of 6,9-dihydroxy-10,11-dihydrodibenz[b,f]oxepin-10-one (Compound 7)

The same procedures as in the steps 1 to 7 of Example 1 were carried out except for the use of 2-chloro-4-hydroxybenzaldehyde in place of 5-bromovaniline in the step 1 of Example 1, to recover 6,9-dihydroxy-10,11-dihydrodibenz[b,f]oxepin-10-one (Compound 7) represented by the following formula in yellow plates.

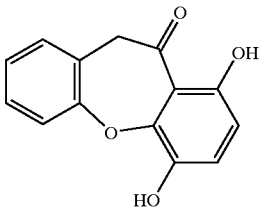

Compound 7

The Compound 7 has a melting point of 182.5 to 184.0° C. By $^1$H-NMR (90 MHz, CDCl$_3$), the Compound 7 has the peaks shown below.

δ(ppm)
4.15(2H, s, Ar—C$\underline{H_2}$)
5.81(1H, brs, O$\underline{H}$)
6.67(1H, d, J=9.1 Hz. Ar—$\underline{H}$)
7.22(1H, d, J=9.1 Hz. Ar—$\underline{H}$)
7.2–7.4(4H, m, Ar—$\underline{H}$)
11.92(1H, s, O$\underline{H}$)

PRODUCTION EXAMPLE 8

Production of 6,7-dihydroxy-10,11-dihydrodibenz[b,f]oxepin-10-one (Compound 8)

Step 1

Amyl alcohol (44 ml) was added to 2,3-dimethoxyphenol (5 g), 2'-bromoacetophenone (7 g), potassium carbonate (6.7 g) and copper acetate (1.1 g), followed by heating and stirring at 150° C. for 8 hours. To the reaction solution was added ethyl acetate (300 ml), and the resulting solution was washed in dilute hydrochloric acid, in water, and in an aqueous saturated sodium chloride solution, and dried over anhydrous magnesium sulfate, and the solvents therein were distilled off under reduced pressure. The residue was purified by silica gel column chromatography (developing solvent:hexane:ethyl acetate=8:1), to recover 2-(2,3-dimethoxyphenoxy)acetophenone (7.6 g; yield of 87%). By $^1$H-NMR (90 MHz, CDCl$_3$), the compound has the peaks shown below.

δ(ppm)
2.73(3H, s, CH$_3$)
3.78(3H, s, OCH$_3$)
3.91(3H, s, OCH$_3$)
6.6–7.9(7H, m, Ar—H)

Step 2

To 2-(2,3-dimethoxyphenoxy)acetophenone (7.6 g) produced in the step 1 were added sulfur (2.7 g) and morpholine (3.7 ml), followed by heating and stirring at 150° C. for 10 minutes and subsequent addition of p-toluenesulfonic acid (0.15 g) for 8-hours heating at 150° C. under stirring. Ethyl acetate (300 ml) and dilute hydrochloric acid (100 ml) were added to the resulting mixture for partition. The organic phase was washed in water and then in an aqueous saturated sodium chloride solution and dried over anhydrous magnesium sulfate, and the solvents were distilled off under reduced pressure. To the resulting residue were added conc. hydrochloric acid (100 ml) and conc. acetic acid (100 ml), prior to stirring at 150° C. for 8 hours, followed by addition of ethyl acetate (300 ml) and water (100 ml), separation of the organic phase, and washing of the organic phase in water and in an aqueous saturated sodium chloride solution. The resulting matter was dried over anhydrous magnesium sulfate, to distill off the solvents therein under reduced pressure. To the resulting residue was added methanesulfonic acid (100 ml), for stirring at room temperature for 3 days, followed by addition of ethyl acetate (300 ml) and washing in water and in an aqueous saturated sodium chloride solution. Subsequently, the resulting matter was dried over anhydrous magnesium sulfate, and the solvents were distilled off under reduced pressure. The resulting residue was purified by silica gel column chromatography (developing solvent:hexane:ethyl acetate=5:1), to recover 6,7-dimethoxy-10,11-dihydrodibenz[b,f]oxepin-10-one (2.8 g; yield of 37%). By $^1$H-NMR (90 MHz, CDCl$_3$), the compound has the peaks shown below.

δ(ppm)
3.94(3H, s, OCH$_3$)
4.04(3H, s, OCH$_3$)
4.08(2H, s, Ar—CH$_2$)
6.77(1H, d, J=9.2 Hz, Ar—H)
7.2–7.4(4H, m, Ar—H)
7.83(1H, d, J=9.2 Hz, Ar—H)

Step 3

6,7-Dimethoxy-10,11-dihydrodibenz[b,f]oxepin-10-one (2.8 g) produced in the step 2 was placed in a pressure-resistant reaction vessel, followed by addition of pyridine hydrochloride salt (28 g), heating and stirring at 200° C. for 1.5 hours, and partition with ethyl acetate and water. The resulting organic phase was washed in dilute hydrochloric acid and in water and subsequently in an aqueous saturated sodium chloride solution, and dried over anhydrous magnesium sulfate, and the solvents were distilled off under reduced pressure. The resulting residue was purified by silica gel column chromatography (developing solvent:hexane:ethyl acetate=1:1) and recrystallized in hexane and ethyl acetate, to recover 6,7-dihydroxy-10,11-dihydrodibenz[b,f] oxepin-10-one (Compound 8) represented by the following formula in colorless needles (1.9 g; yield of 77%).

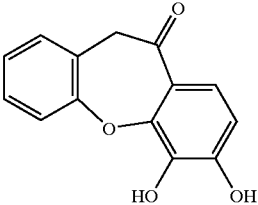

Compound 8

The Compound 8 has a melting point of 180.7 to 182.4° C. By $^1$H-NMR (90 MHz, DMSO-d$_6$), the Compound 8 has the peaks shown below.

δ(ppm)
4.04(2H, s, Ar—CH$_2$)
6.69(1H, d, J=8.8 Hz, Ar—H)
7.2–7.6(5H, m, Ar—H)

PRODUCTION EXAMPLE 9

Production of 7,8,9-trihydroxy-10,11-dihydrodibenz [b,f]oxepin-10-one (Compound 9)

The same procedures as in the steps 1 to 3 of Example 8 were carried out except for the use of 3,4,5-trimethoxyphenol in place of 2,3-dimethoxyphenol in the step 1 of Example 8, to recover 7,8,9-trihydroxy-10,11-dihydrodibenz[b,f]oxepin-10-one (Compound 9) represented by the following formula in pale yellow needles.

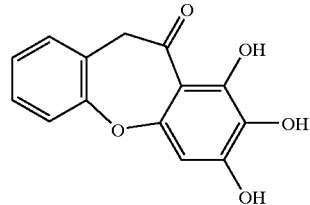

Compound 9

The Compound 9 has a melting point of 166.5 to 168.5° C. By $^1$H-NMR (90 MHz, CDCl$_3$), the Compound 9 has the peaks shown below.

δ(ppm)
4.08(2H, s, Ar—CH$_2$)
5.31(1H, brs, OH)
6.07(1H, brs, OH)
6.53(1H, s, Ar—H)
7.2–7.4(4H, m, Ar—H)
13.05(1H, s, OH)

PRODUCTION EXAMPLE 10

Production of 6,7,8-trihydroxy-10,11-dihydrodibenz [b,f]oxepin-10-one (Compound 10)

2,3,4-Trimethoxybenzaldehyde (5 g) was suspended in anhydrous methylene chloride (50 ml), followed by addition of m-chloroperbenzoic acid (10 g; purity of 70%) to heat and stir the resulting mixture at 50° C. for 3 hours. After distilling off the solvents under reduced pressure, the residue was dissolved in ethyl acetate (100 ml) and washed in an aqueous saturated sodium hydrogen carbonate solution, in water and in an aqueous saturated sodium chloride solution, and dried over anhydrous magnesium sulfate. Then, the solvents were distilled off under reduced pressure. To the residue were added dioxane (15 ml) and a 3N sodium hydroxide solution (15 ml), prior to stirring at room temperature for 30 minutes and adjustment to acidity with dilute hydrochloric acid, followed by ethyl acetate extraction three times. The organic phase was washed in water and in an aqueous saturated sodium chloride solution and dried over anhydrous magnesium sulfate, followed by distillation of the solvents under reduced pressure. The residue was purified by silica gel column chromatography (developing solvent:hexane:ethyl acetate=3:1), to recover 2,3,4-trimethoxyphenol (2.4 g; yield of 51%). By $^1$H-NMR (90 MHz, CDCl$_3$), the compound has the peaks shown below.

δ(ppm)

3.81(3H, s, OC$\underline{H}_3$)

3.89(3H, s, OC$\underline{H}_3$)

3.96(3H, s, OC$\underline{H}_3$)

6.54(1H, d, J=8.5 Hz, Ar—$\underline{H}$)

6.66(1H, d, J=8.5 Hz, Ar—$\underline{H}$)

The same procedures as in the steps 1 to 3 of Example 8 were carried out except for the use of the above compound in place of 2,3-dimethoxyphenol in the step 1 of Example 8, to recover 6,7,8-trihydroxy-10,11-dihydrodibenz[b,f]oxepin-10-one (Compound 10) represented by the following formula in skin-colored amorphous powder.

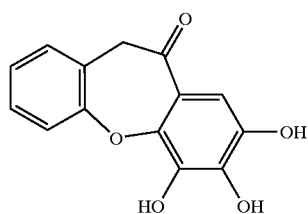

Compound 10

The Compound 10 has a melting point of 193.3 to 195.3° C. By $^1$H-NMR (90 MHz, DMSO-d$_6$), the Compound 10 has the peaks shown below.

δ(ppm)

3.99(2H, s, C$\underline{H}_2$)

6.85(1H, s, Ar—$\underline{H}$)

7.2–7.5(4H, m, Ar—$\underline{H}$)

PRODUCTION EXAMPLE 11

Production of 7,9-dihydroxy-10,11-dihydrodibenz[b,f]oxepin-10-one (Compound 11)

The same procedures as in the steps 1 to 3 of Example 8 were carried out except for the use of 3,5-dimethoxyphenol in place of 2,3-dimethoxyphenol in the step 1 of Example 8, to recover 7,9-dihydroxy-10,11-dihydrodibenz[b,f]oxepin-10-one (Compound 11) represented by the following formula in pale yellow needles.

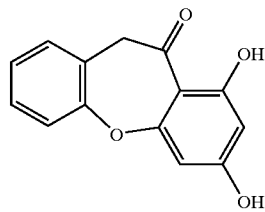

Compound 11

The Compound 11 has a melting point of 191.5 to 193.5° C. By $^1$H-NMR (90 MHz, DMSO-d$_6$), the Compound 11 has the peaks shown below.

δ(ppm)

4.13(2H, s, Ar—C$\underline{H}_2$)

6.14(1H, d, J=2.4 Hz, Ar—$\underline{H}$)

6.42(1H, d, J=2.4 Hz, Ar—$\underline{H}$)

7.2–7.6(4H, m, Ar—$\underline{H}$)

13.04(1H, s, O$\underline{H}$)

PRODUCTION EXAMPLE 12

Production of 10,11-dihydrodibenz[b,f]oxepin-1,3-diol (Compound 12)

Step 1

The same procedures as in the steps 1 and 2 of Example 8 were carried out except for the use of 3,5-dimethoxyphenol in place of 2,3-dimethoxyphenol in the step 1 of Example 8, to recover 7,9-dimethoxy-10,11-dihydrodibenz[b,f]oxepin-10-one (0.72 g). Anhydrous methanol (5 ml) was added to the above compound, which was then stirred at 0° C. in argon atmosphere. To the stirred mixture was added sodium boron hydride (0.2 g), followed by stirring at room temperature for one hour. The resulting solution was adjusted to acidity with dilute hydrochloric acid and extracted with ethyl acetate three times. The resulting organic phase was washed in water and in an aqueous saturated sodium chloride solution, and dried over anhydrous magnesium sulfate. Then, the solvents were distilled off under reduced pressure.

Step 2

The residue was placed in a pressure-resistant reaction vessel, followed by addition of pyridine hydrochloride salt (3 g) and stirring at 200° C. for 1.5 hours. Ethyl acetate and water were added to the resulting mixture for partition, and the resulting organic phase was washed in dilute hydrochloric acid and in water, and subsequently in an aqueous saturated sodium chloride solution, and dried over anhydrous magnesium sulfate. The solvents were distilled off under reduced pressure.

Step 3

To an ethyl acetate solution of the residue was added catalyst platinum dioxide, stirred under hydrogen atmosphere and the resulting product was purified by silica gel column chromatography (developing solvent:ethyl acetate:hexane=1:2) and recrystallized in chloroform and hexane, to yield 10,11-dihydrodibenz[b,f]oxepin-1,3-diol (Compound 12) represented by the following formula in skin-colored amorphous powder (240 mg; yield of 40%).

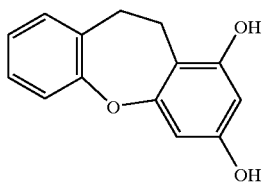

Compound 12

The Compound 12 has a melting point of 145.3 to 147.2° C. By $^1$H-NMR (90 MHz, CDCl$_3$), the Compound 12 has the peaks shown below.

δ(ppm)
2.8–3.0(2H, m, C$\underline{H}_2$)
3.1–3.3(2H, m, C$\underline{H}_2$)
4.73(1H, brs, O$\underline{H}$)
4.81(1H, brs, O$\underline{H}$)
6.08(1H, d, J=2.4 Hz, Ar—$\underline{H}$)
6.31(1H, d, J=2.4 Hz, Ar—$\underline{H}$)
7.0–7.2(4H, m, Ar—$\underline{H}$)

PRODUCTION EXAMPLE 13

Production of 7,8-dihydroxy-10,11-dihydrodibenz[b,f]oxepin-10-one (Compound 13)

The same procedures as in the steps 1 to 3 of Example 8 were carried out except for the use of 3,4-dimethoxyphenol in place of 2,3-dimethoxyphenol in the step 1 of Example 8, to recover 7,8-dihydroxy-10,11-dihydrodibenz[b,f]oxepin-10-one (Compound 13) represented by the following formula in pale yellow plates.

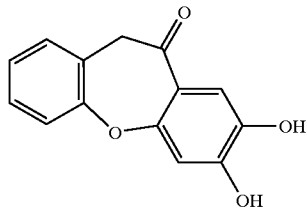

Compound 13

The Compound 13 has a melting point of 198.1 to 200.4° C. By $^1$H-NMR (90 MHz, DMSO-d$_6$), the Compound 13 has the peaks shown below.

δ(ppm)
3.99(2H, s, Ar—C$\underline{H}_2$)
6.78(1H, s, Ar—$\underline{H}$)
7.1–7.4(5H, m, Ar—$\underline{H}$)

PRODUCTION EXAMPLE 14

Production of 10,11-dihydrodibenz[b,f]oxepin-2,3-diol (Compound 14)

The same procedures as in the steps 1 to 3 of Example 12 were carried out except for the use of 7,8-dimethoxy-10,11-dihydrodibenz[b,f]oxepin-10-one produced in the step 2 of Example 13 as a starting material in the process of Example 12, to recover 10,11-dihydrodibenz[b,f]oxepin-2,3-diol (Compound 14) represented by the following formula in colorless plates.

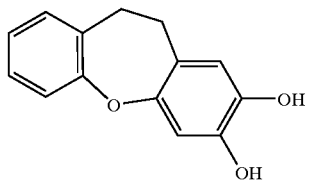

Compound 14

The Compound 14 has a melting point of 150.6 to 152.6° C. By $^1$H-NMR (90 MHz, CDCl$_3$), the Compound 14 has the peaks shown below.

δ(ppm)
2.9–3.2(2H, m, C$\underline{H}_2$)
2.9–3.2(2H, m, C$\underline{H}_2$)
4.8–5.2(1H, brs, O$\underline{H}$)
6.61(1H, s, Ar—$\underline{H}$)
6.73(1H, s, Ar—$\underline{H}$)
6.9–7.2(4H, m, Ar—$\underline{H}$)

PRODUCTION EXAMPLE 15

Production of 3-chloro-7,9-dihydroxy-10,11-dihydrodibenz[b,f]oxepin-10-one (Compound 15)

The same procedures as in the steps 1 to 3 of Example 8 were carried out except for the use of 3,5-dimethoxyphenol and 2',4'-dichloroacetophenone in place of 2,3-dimethoxyphenol and 2'-bromoacetophenone, respectively, in the step 1 of Example 8, to recover 3-chloro-7,9-dihydroxy-10,11-dihydrodibenz[b,f]oxepin-10-one (Compound 15) represented by the following formula in colorless needles.

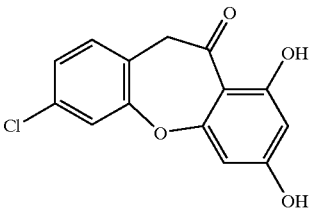

Compound 15

The Compound 15 has a melting point of 236.5 to 238.5° C. By $^1$H-NMR (90 MHz, DMSO-d$_6$), the Compound 15 has the peaks shown below.

δ(ppm)
4.12(2H, s, Ar—C$\underline{H}_2$)
6.11(1H, d, J=2.4 Hz, Ar—$\underline{H}$)
6.40(1H, d, J=2.4 Hz, Ar—$\underline{H}$)
7.3–7.5(3H, m, Ar—$\underline{H}$)
12.98(1H, s, O$\underline{H}$)

PRODUCTION EXAMPLE 16

Production of 7-chloro-10,11-dihydrodibenz[b,f]oxepin-1,3-diol (Compound 16)

The same procedures as in Example 12 were carried out except for the use of 3-chloro-7,9-dimethoxy-10,11-dihydrodibenz[b,f]oxepin-10-one produced in the step 2 of Example 15 as a starting material in the process of Example 12, to recover 7-chloro-10,11-dihydrodibenz[b,f]oxepin-1, 3-diol (Compound 16) represented by the following formula in skin-colored plates.

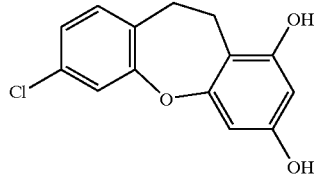
Compound 16

The Compound 16 has a melting point of 185.5 to 187.5° C. By ¹H-NMR (90 MHz, DMSO-$d_6$), the Compound 16 has the peaks shown below.
δ(ppm)
2.6–2.8(2H, m, C$\underline{H}_2$)
2.8–3.1(2H, m, C$\underline{H}_2$)
6.0–6.2(2H, m, Ar—$\underline{H}$)
7.1–7.3(3H, m, Ar—$\underline{H}$)
9.3(1H, br, O$\underline{H}$)
9.4(1H, br, O$\underline{H}$)

PRODUCTION EXAMPLE 17

Production of 3-chloro-7,8-dihydroxy-10,11-dihydrodibenz[b,f]oxepin-10-one (Compound 17)

The same procedures as in the steps 1 to 3 of Example 8 were carried out except for the use of 3,4-dimethoxyphenol and 2',4'-dichloroacetophenone in place of 2,3-dimethoxyphenol and 2'-bromoacetophenone, respectively, in the step 1 of Example 8, to recover 3-chloro-7,8-dihydroxy-10,11-dihydrodibenz[b,f]oxepin-10-one (Compound 17) represented by the following formula in mud yellow needles.

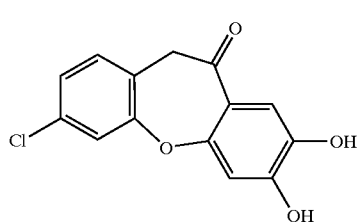
Compound 17

The Compound 17 has a melting point of 248.1 to 250.1° C. By ¹H-NMR (90 MHz, DMSO-$d_6$), the Compound 17 has the peaks shown below.
δ(ppm)
4.00(2H, s, Ar—C$\underline{H}_2$)
6.80(1H, s, Ar—$\underline{H}$)
7.32(1H, s, Ar—$\underline{H}$)
7.3–7.5(3H, m, Ar—$\underline{H}$)

PRODUCTION EXAMPLE 18

Production of 7-chloro-10,11-dihydrodibenz[b,f]oxepin-2,3-diol (Compound 18)

The same procedures as in Example 12 were carried out except for the use of 3-chloro-7,8-dimethoxy-10,11-dihydrodibenz[b,f]oxepin-10-one produced in the step 2 of Example 17 as a starting material in the process of Example 12, to recover 7-chloro-10,11-dihydrodibenz[b,f]oxepin-2,3-diol (Compound 18) represented by the following formula in colorless needles.

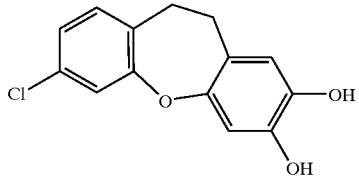
Compound 18

The Compound 18 has a melting point of 119.9 to 121.9° C. By ¹H-NMR (90 MHz, CDCl$_3$), the Compound 18 has the peaks shown below.
δ(ppm)
2.9–3.1(2H, m, C$\underline{H}_2$)
2.9–3.1(2H, m, C$\underline{H}_2$)
5.01(1H, brs, O$\underline{H}$)
6.62(1H, s, Ar—$\underline{H}$)
6.71(1H, s, Ar—$\underline{H}$)
7.0–7.2(3H, m, Ar—$\underline{H}$)

PRODUCTION EXAMPLE 19

Production of 2-chloro-7,9-dihydroxy-10,11-dihydrodibenz[b,f]oxepin-10-one (Compound 19)

The same procedures as in the steps 1 to 3 of Example 8 were carried out except for the use of 3,5-dimethoxyphenol and 2',5'-dichloroacetophenone in place of 2,3-dimethoxyphenol and 2'-bromoacetophenone, respectively, in the step 1 of Example 8, to recover 2-chloro-7,9-dihydroxy-10,11-dihydrodibenz[b,f]oxepin-10-one (Compound 19) represented by the following formula in colorless needles.

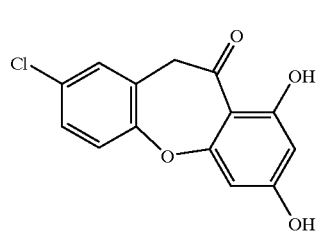
Compound 19

The Compound 19 has a melting point of 183.1 to 184.2° C. By ¹H-NMR (90 MHz, DMSO-$d_6$), the Compound 19 has the peaks shown below.
δ(ppm)
4.14(2H, s, Ar—C$\underline{H}_2$)
6.11(1H, d, J=2.4 Hz, Ar—$\underline{H}$)
6.39(1H, d, J=2.4 Hz, Ar—$\underline{H}$)
7.3–7.4(2H, m, Ar—$\underline{H}$)
7.5–7.6(1H, m, Ar—$\underline{H}$)
12.97(1H, s, O$\underline{H}$)

PRODUCTION EXAMPLE 20

Production of 8-chloro-10,11-dihydrodibenz[b,f]oxepin-1,3-diol (Compound

The same procedures as in Example 12 were carried out except for the use of 2-chloro-7,9-dimethoxy-10,11- dihydrodibenz[b,f]oxepin-10-one produced in the step 2 of Example 19 as a starting material in the process of Example 12, to recover 8-chloro-10,11-dihydrodibenz[b,f]oxepin-1,3-diol (Compound 20) represented by the following formula in pale orange needles.

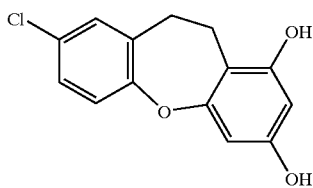

Compound 20

The Compound 20 has a melting point of 166.2 to 168.2° C. By ¹H-NMR (90 MHz, DMSO-$d_6$), the Compound 20 has the peaks shown below.
δ(ppm)
2.7–2.9(2H, m, C$\underline{H}_2$)
2.9–3.1(2H, m, C$\underline{H}_2$)
6.0–6.2(2H, m, Ar—$\underline{H}$)
7.1–7.3(3H, m, Ar—$\underline{H}$)
9.2(1H, br, O$\underline{H}$)
9.4(1H, br, O$\underline{H}$)

PRODUCTION EXAMPLE 21

Production of 2-chloro-7,8-dihydroxy-10,11-dihydrodibenz[b,f]oxepin-10-one (Compound 21)

The same procedures as in the steps 1 to 3 of Example 8 were carried out except for the use of 3,4-dimethoxyphenol and 2',5'-dichloroacetophenone in place of 2,3-dimethoxyphenol and 2'-bromoacetophenone, respectively, in the step 1 of Example 8, to recover 2-chloro-7,8-dihydroxy-10,11-dihydrodibenz[b,f]oxepin-10-one (Compound 21) represented by the following formula in orange needles.

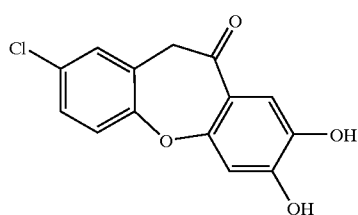

Compound 21

The Compound 21 has a melting point of 236.0 to 238.0° C. By 1H-NMR (90 MHz, DMSO-$d_6$) the Compound 21has the peaks shown below.
δ(ppm)
4.00(2H, s, Ar—C$\underline{H}_2$)
6.77(1H, s, Ar—$\underline{H}$)
7.26(1H, s, Ar—$\underline{H}$)
7.3–7.6(3H, m, Ar—$\underline{H}$)

PRODUCTION EXAMPLE 22

Production of 8-chloro-10,11-dihydrodibenz[b,f]oxepin-2,3-diol (Compound 22)

The same procedures as in Example 12 were carried out except for the use of 2-chloro-7,8-dimethoxy-10,11-dihydrodibenz[b,f]oxepin-10-one produced in the step 2 of Example 21 as a starting material in the process of Example 12, to recover 8-chloro-10,11-dihydrodibenz[b,f]oxepin-2,3-diol (Compound 22) represented by the following formula in yellow plates.

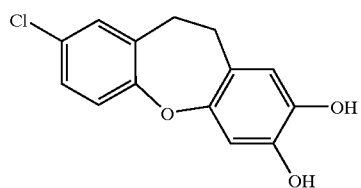

Compound 22

The Compound 22 has a melting point of 168.2 to 170.2° C. By ¹H-NMR (90 MHz, DMSO-$d_6$), the Compound 22 has the peaks shown below.
δ(ppm)
2.7–3.1(2H, m, C$\underline{H}_2$)
2.7–3.1(2H, m, C$\underline{H}_2$)
6.51(1H, s, Ar—$\underline{H}$)
6.55(1H, s, Ar—$\underline{H}$)
7.0–7.4(3H, m, Ar—$\underline{H}$)
8.8(1H, brs, O$\underline{H}$)
8.8(1H, brs, O$\underline{H}$)

PRODUCTION EXAMPLE 23

Production of 3-fluoro-7,9-dihydroxy-10,11-dihydrodibenz[b,f]oxepin-10-one (Compound 23)

The same procedures as in the steps 1 to 3 of Example 8 were carried out except for the use of 3,5-dimethoxyphenol and 2',4'-difluoroacetophenone in place of 2,3-dimethoxyphenol and 2'-bromoacetophenone, respectively, in the step 1 of Example 8, to recover 3-fluoro-7,9-dihydroxy-10,11-dihydrodibenz[b,f]oxepin-10-one (Compound 23) represented by the following formula in mud yellow plates.

Compound 23

The Compound 23 has a melting point of 178.5 to 180.5° C. By ¹H-NMR (90 MHz, DMSO-$d_6$), the Compound 23 has the peaks shown below.
δ(ppm)
4.10(2H, s, Ar—C$\underline{H}_2$)
6.10(1H, d, J=2.3 Hz, Ar—$\underline{H}$)
6.38(1H, d, J=2.3 Hz, Ar—$\underline{H}$)
7.0–7.6(3H, m, Ar—$\underline{H}$)
12.99(1H, s, O$\underline{H}$)

PRODUCTION EXAMPLE 24

Production of 7-fluoro-10,11-dihydrodibenz[b,f]oxepin-1,3-diol (Compound 24)

The same procedures as in Example 12 were carried out except for the use of 7,9-dimethoxy-3-fluoro-10,11- dihydrodibenz[b,f]oxepin-10-one produced in the step 2 of Example 23 as a starting material in the process of Example 12, to recover 7-fluoro-10,11-dihydrodibenz[b,f]oxepin-1,3-diol (Compound 24) represented by the following formula in colorless needles.

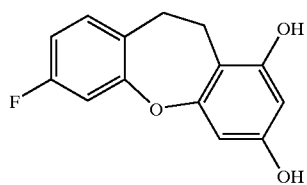

Compound 24

The Compound 24 has a melting point of 177.7 to 179.7° C. By $^1$H-NMR (90 MHz, DMSO-$d_6$), the Compound 24 has the peaks shown below.

δ(ppm)
2.5–2.8(2H, m, C$\underline{H_2}$)
2.9–3.1(2H, m, C$\underline{H_2}$)
6.07(1H, d, J=2.3 Hz, Ar—$\underline{H}$)
6.12(1H, d, J=2.3 Hz, Ar—$\underline{H}$)
6.8–7.4(3H, m, Ar—$\underline{H}$)
9.2–9.5(1H, br, O$\underline{H}$)

PRODUCTION EXAMPLE 25

Production of 3-fluoro-7,8-dihydroxy-10,11-dihydrodibenz[b,f]oxepin-10-one (Compound 25)

The same procedures as in the steps 1 to 3 of Example 8 were carried out except for the use of 3,4-dimethoxyphenol and 2',4'-difluoroacetophenone in place of 2,3-dimethoxyphenol and 2'-bromoacetophenone, respectively, in the step 1 of Example 8, to recover 3-fluoro-7,8-dihydroxy-10,11-dihydrodibenz[b,f]oxepin-10-one (Compound 25) represented by the following formula in colorless needles.

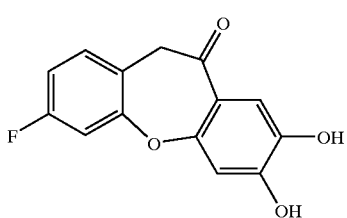

Compound 25

The Compound 25 has a melting point of 195.1 to 197.1° C. By $^1$H-NMR (90 MHz, DMSO-$d_6$), the Compound 25 has the peaks shown below.

δ(ppm)
3.99(2H, s, Ar—C$\underline{H_2}$)
6.80(1H, s, Ar—$\underline{H}$)
6.9–7.5(3H, m, Ar—$\underline{H}$)
7.28(1H, s, Ar—$\underline{H}$)

PRODUCTION EXAMPLE 26

Production of 7-fluoro-10,11-dihydrodibenz[b,f]oxepin-2,3-diol (Compound 26)

The same procedures as in Example 12 were carried out except for the use of 7,8-dimethoxy-3-fluoro-10,11-dihydrodibenz[b,f]oxepin-10-one produced in the step 2 of Example 25 as a starting material in the process of Example 12, to recover 7-fluoro-10,11-dihydrodibenz[b,f]oxepin-2,3-diol (Compound 26) represented by the following formula in pale mud yellow plates.

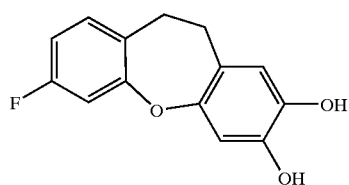

Compound 26

The Compound 26 has a melting point of 105.8 to 107.4° C. By $^1$H-NMR (90 MHz, CDCl$_3$) the Compound 26 has the peaks shown below.

δ(ppm)
2.9–3.1(2H, m, C$\underline{H_2}$)
2.9–3.1(2H, m, C$\underline{H_2}$)
6.62(1H, s, Ar—$\underline{H}$)
6.71(1H, s, Ar—$\underline{H}$)
6.7–7.1(3H, m, Ar—$\underline{H}$)

PRODUCTION EXAMPLE 27

Production of 3,4-dichloro-7,9-dihydroxy-10,11-dihydrodibenz[b,f]oxepin-10-one (Compound 27)

The same procedures as in the steps 1 to 3 of Example 8 were carried out except for the use of 3,5-dimethoxyphenol and 2',3',4'-trichloroacetophenone in place of 2,3-dimethoxyphenol and 2'-bromoacetophenone, respectively, in the step 1 of Example 8, to recover 3,4-dichloro-7,9-dihydroxy-10,11-dihydrodibenz[b,f]oxepin-10-one (Compound 27) represented by the following formula in yellow plates.

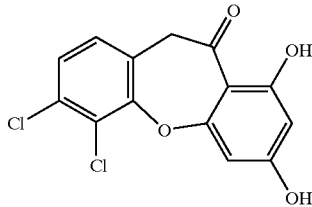

Compound 27

The Compound 27 has a melting point of 222.2 to 224.2° C. By $^1$H-NMR (90 MHz, DMSO-$d_6$), the Compound 27 has the peaks shown below.

δ(ppm)
4.20(2H, s, Ar—C$\underline{H_2}$)
6.13(1H, d, J=2.4 Hz, Ar—$\underline{H}$)
6.48(1H, d, J=2.4 Hz, Ar—$\underline{H}$)
7.4–7.5(2H, m, Ar—$\underline{H}$)
12.90(1H, s, O$\underline{H}$)

PRODUCTION EXAMPLE 28

Production of 6,7-dichloro-10,11-dihydrodibenz[b,f]oxepin-1,3-diol (Compound 28)

The same procedures as in Example 12 were carried out except for the use of 3,4-dichloro-7,9-dimethoxy-10,11- dihydrodibenz[b,f]oxepin-10-one produced in the step 2 of Example 27 as a starting material in the process of Example 12, to recover 6,7-dichloro-10,11-dihydrodibenz[b,f]oxepin-1,3-diol (Compound 28) represented by the following formula in colorless needles.

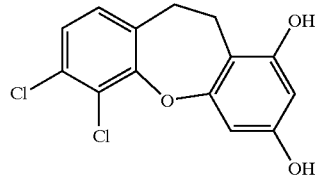

Compound 28

The Compound 28 has a melting point of 172.2 to 174.0° C. By $^1$H-NMR (90 MHz, DMSO-$d_6$), the Compound 28 has the peaks shown below.

δ(ppm)
2.6–2.8(2H, m, C$\underline{H}_2$)
3.0–3.2(2H, m, C$\underline{H}_2$)
6.14(1H, d, J=2.5 Hz, Ar—$\underline{H}$)
6.21(1H, d, J=2.5 Hz, Ar—$\underline{H}$)
7.25(1H, d, J=8.3 Hz, Ar—$\underline{H}$)
7.38(1H, d, J=8.3 Hz, Ar—$\underline{H}$)
9.3–9.6(1H, br, O$\underline{H}$)
9.3–9.6(1H, br, O$\underline{H}$)

PRODUCTION EXAMPLE 29

Production of 2-fluoro-7,9-dihydroxy-10,11-dihydrodibenz[b,f]oxepin-10-one (Compound 29)

A solution of 2,5-difluorobenzaldehyde (24.6 g) in tetrahydrofuran (100 ml) was added dropwise to an ice-cooled solution (207 ml) of 0.92N magnesium methylbromide in tetrahydrofuran. The resulting solution was stirred at room temperature for 1.5 hours, and the organic phase was washed in an aqueous saturated sodium chloride solution and dried over anhydrous magnesium sulfate, to subsequently distill off the solvents under reduced pressure. To the residue were added anhydrous dichloromethane (500 ml), sodium acetate (14.2 g) and pyridinium chlorochromate (55.94 g), prior to stirring at room temperature for 10 hours. To the resulting mixture was added an aqueous saturated sodium hydrogen carbonate solution, prior to extraction in ethyl acetate three times. The organic phase was washed in water and in an aqueous saturated sodium chloride solution and dried over anhydrous magnesium sulfate, to distill off the solvents under reduced pressure. The residue was purified by silica gel column chromatography (developing solvent:hexane-:ethyl acetate=85:15), to recover 2',5'-difluoroacetophenone (22.73 g; yield of 84%). By $^1$H-NMR (90 MHz, CDCl$_3$), the compound has the peaks shown below.

δ(ppm)
2.63(3H, d, $^5J_{HF}$=5 Hz, C$\underline{H}_3$)
7.1–7.2(2H, m, Ar—$\underline{H}$)
7.4–7.5(1H, m, Ar—$\underline{H}$)

The same procedures as in the steps 1 to 3 of Example 8 were carried out except for the use of the compound in place of 2'-bromoacetophenone and the use of 3,5-dimethoxyphenol in place of 2,3-dimethoxyphenol in the step 1 of Example 8, to recover 2-fluoro-7,9-dihydroxy-10, 11-dihydrodibenz[b,f]oxepin-10-one (Compound 29) represented by the following formula in pale yellow needles.

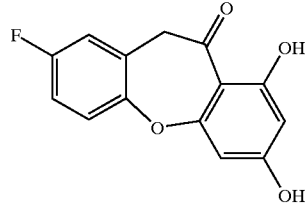

Compound 29

The Compound 29 has a melting point of 162.9 to 164.0° C. By $^1$H-NMR (90 MHz, DMSO-$d_6$), the Compound 29 has the peaks shown below.

δ(ppm)
4.10(2H, s, Ar—C$\underline{H}_2$)
6.08(1H, d, J=2 Hz, Ar—$\underline{H}$)
6.35(1H, d, J=2 Hz, Ar—$\underline{H}$)
7.1–7.4(3H, m, Ar—$\underline{H}$)
11.1(1H, br, O$\underline{H}$)
12.94(1H, s, O$\underline{H}$)

PRODUCTION EXAMPLE 30

Production of 8-fluoro-10,11-dihydrodibenz[b,f] oxepin-1,3-diol (Compound 30)

The same procedures as in Example 12 were carried out except for the use of 2-fluoro-7,9-dimethoxy-10,11-dihydrodibenz[b,f]oxepin-10-one produced in the step 2 of Example 29 as a starting material in the process of Example 12, to recover 8-fluoro-10,11-dihydrodibenz[b,f]oxepin-1,3-diol (Compound 30) represented by the following formula in colorless amorphous powder.

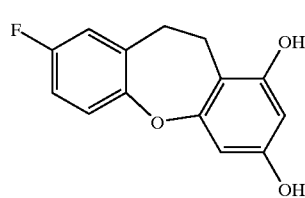

Compound 30

The Compound 30 has a melting point of 148.2 to 150.5° C. By $^1$H-NMR (90 MHz, CDCl$_3$), the Compound 30 has the peaks shown below.

δ(ppm)
2.7–2.8(2H, m, C$\underline{H}_2$)
2.9–3.0(2H, m, C$\underline{H}_2$)
6.0–6.1(2H, m, Ar—$\underline{H}$)
7.0–7.1(3H, m, Ar—$\underline{H}$)
9.17(1H, s, O$\underline{H}$)
9.37(1H, s, O$\underline{H}$)

PRODUCTION EXAMPLE 31

Production of 2-fluoro-7,8-dihydroxy-10,11-dihydrodibenz[b,f]oxepin-10-one (Compound 31)

The same procedures as in the steps 1 to 3 of Example 29 were carried out except for the use of 3,4-dimethoxyphenol in place of 3,5-dimethoxyphenol in the process of Example 29, to recover 2-fluoro-7,8-dihydroxy-10,11-dihydrodibenz

[b,f]oxepin-10-one (Compound 31) represented by the following formula in colorless needles.

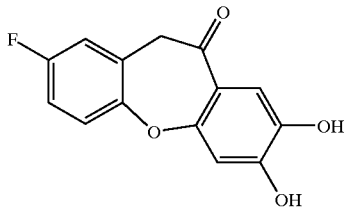

Compound 31

The Compound 31 has a melting point of 226.5 to 228.5° C. By $^1$H-NMR (90 MHz, DMSO-$d_6$), the Compound 31 has the peaks shown below.

δ(ppm)
3.99(2H, s, Ar—C$\underline{H}_2$)
6.77(1H, s, Ar—$\underline{H}$)
6.9–7.0(4H, m, Ar—$\underline{H}$)
9.74(1H, br, O$\underline{H}$)
9.74(1H, br, O$\underline{H}$)

PRODUCTION EXAMPLE 32

Production of 8-fluorodibenz[b,f]oxepin-2,3-diol (Compound 32)

The same procedures as in the steps 1 and 2 of Example 12 were carried out except for the use of 2-fluoro-7,8-dimethoxy-10,11-dihydrodibenz[b,f]oxepin-10-one produced in the step 2 of Example 31 as a starting material in the process of Example 12, to recover 8-fluorodibenz[b,f]oxepin-2,3-diol (Compound 32) represented by the following formula in colorless plates.

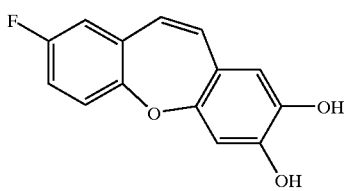

Compound 32

The Compound 32 has a melting point of 207.0 to 209.0° C. By $^1$H-NMR (90 MHz, DMSO-$d_6$), the Compound 32 has the peaks shown below.

δ(ppm)
6.49(1H, d, J=11 Hz, C$\underline{H}$)
6.61(1H, d, J=11 Hz, C$\underline{H}$)
6.66(1H, s, Ar—$\underline{H}$)
6.66(1H, s, Ar—$\underline{H}$)
7.0–7.2(3H, m, Ar—$\underline{H}$)
9.16(1H, br, O$\underline{H}$)
9.16(1H, br, O$\underline{H}$)

PRODUCTION EXAMPLE 33

Production of 8-fluoro-10,11-dihydrodibenz[b,f]oxepin-2,3-diol (Compound 33)

The same procedures as in the steps 1 to 3 of Example 12 were carried out except for the use of 2-fluoro-7,8-dimethoxy-10,11-dihydrodibenz[b,f]oxepin-10-one produced in the step 2 of Example 31 as a starting material in the process of Example 12, to recover 8-fluoro-10,11-dihydrodibenz[b,f]oxepin-2,3-diol (Compound 33) represented by the following formula in colorless plates.

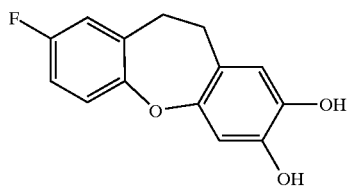

Compound 33

The Compound 33 has a melting point of 148.0 to 151.0° C. By $^1$H-NMR (90 MHz, DMSO-$d_6$), the Compound 33 has the peaks shown below.

δ(ppm)
2.9–3.0(2H, m, C$\underline{H}_2$)
2.9–3.0(2H, m, C$\underline{H}_2$)
6.50(1H, s, Ar—$\underline{H}$)
6.55(1H, s, Ar—$\underline{H}$)
6.8–7.2(3H, m, Ar—$\underline{H}$)
8.64(1H, s, O$\underline{H}$)
8.90(1H, s, O$\underline{H}$)

PRODUCTION EXAMPLE 34

Production of 2.4-dichloro-7,9-dihydroxy-10,11-dihydrodibenz[b,f]oxepin-10-one (Compound 34)

The same procedures as in Example 29 were carried out except for the use of 2,3,5-trichlorobenzaldehyde in place of 2,5-difluorobenzaldehyde in the process of Example 29, to recover 2,4-dichloro-7,9-dihydroxy-10,11-dihydrodibenz[b,f]oxepin-10-one (Compound 34) represented by the following formula in pale red needles.

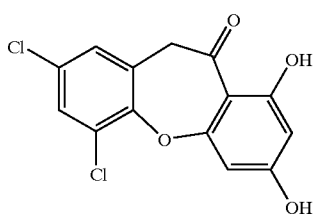

Compound 34

The Compound 34 has a melting point of 224.0 to 225.7° C. By $^1$H-NMR (90 MHz, DMSO-$d_6$), the Compound 34 has the peaks shown below.

δ(ppm)
4.20(2H, s, Ar—C$\underline{H}_2$)
6.14(1H, d, J=2.2 Hz, Ar—$\underline{H}$)
6.44(1H, d, J=2.2 Hz, Ar—$\underline{H}$)
7.60(1H, d, J=2.4 Hz, Ar—$\underline{H}$)
7.67(1H, d, J=2.4 Hz, Ar—$\underline{H}$)

PRODUCTION EXAMPLE 35

Production of 6,8-dichloro-10,11-dihydrodibenz[b,f]oxepin-1,3-diol (Compound 35)

The same procedures as in Example 12 were carried out except for the use of 2,4-dichloro-7,9-dimethoxy-10,11- dihydrodibenz[b,f]oxepin-10-one produced in the step 2 of Example 34 as a starting material in the process of Example 12, to recover 6,8-dichloro-10,11-dihydrodibenz[b,f]oxepin-1,3-diol (Compound 35) represented by the following formula in colorless needles.

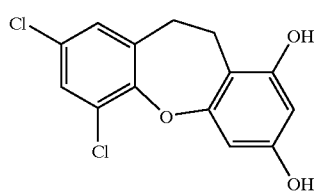

Compound 35

The Compound 35 has a melting point of 160.5 to 161.5° C. By $^1$H-NMR (90 MHz, DMSO-$d_6$), the Compound 35 has the peaks shown below.
δ(ppm)
2.6–2.8(2H, m, C$\underline{H_2}$)
3.0–3.2(2H, m, C$\underline{H_2}$)
6.13(1H, d, J=2.5 Hz, Ar—$\underline{H}$)
6.18(1H, d, J=2.5 Hz, Ar—$\underline{H}$)
7.36(1H, d, J=2.7 Hz, Ar—$\underline{H}$)
7.49(1H, d, J=2.7 Hz, Ar—$\underline{H}$)

PRODUCTION EXAMPLE 36

Production of 4-chloro-7,9-dihydroxy-10,11-dihydrodibenz[b,f]oxepin-10-one (Compound 36)

The same procedures as in Example 29 were carried out except for the use of 2,3-dichlorobenzaldehyde in place of 2,5-difluorobenzaldehyde in the process of Example 29, to recover 4-chloro-7,9-dihydroxy-10,11-dihydrodibenz[b,f]oxepin-10-one (Compound 36) represented by the following formula in colorless needles.

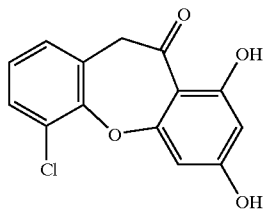

Compoound 36

The Compound 36 has a melting point of 163.0 to 163.8° C. By $^1$H-NMR (90 MHz, DMSO-$d_6$), the Compound 36 has the peaks shown below.
δ(ppm)
4.18(2H, s, Ar—C$\underline{H_2}$)
6.13(1H, d, J=2.4 Hz, Ar—$\underline{H}$)
6.47(1H, d, J=2.4 Hz, Ar—$\underline{H}$)
7.1–7.5(3H, m, Ar—$\underline{H}$)
12.93(1H, s, O$\underline{H}$)

PRODUCTION EXAMPLE 37

Production of 6-chloro-10,11-dihydrodibenz[b,f]oxepin-1,3-diol (Compound 37)

The same procedures as in Example 12 were carried out except for the use of 4-chloro-7,9-dimethoxy-10,11-dihydrodibenz[b,f]oxepin-10-one produced in the step 2 of Example 36 as a starting material in the process of Example 12, to recover 6-chloro-10,11-dihydrodibenz[b,f]oxepin-1,3-diol (Compound 37) represented by the following formula in pale yellow plates.

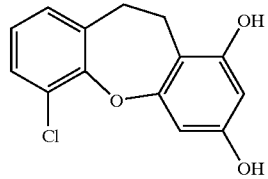

Compound 37

The Compound 37 has a melting point of 202.5 to 203.0° C. By $^1$H-NMR (90 MHz, DMSO-$d_6$), the Compound 37 has the peaks shown below.
δ(ppm)
2.6–2.9(2H, m, C$\underline{H_2}$)
2.9–3.2(2H, m, C$\underline{H_2}$)
6.12(1H, d, J=2.4 Hz, Ar—$\underline{H}$)
6.20(1H, d, J=2.4 Hz, Ar—$\underline{H}$)
7.0–7.4(3H, m, Ar—$\underline{H}$)

PRODUCTION EXAMPLE 38

Production of 7,9-dihydroxy-2-trifluoromethyl-10,11-dihydrodibenz[b,f]oxepin-10-one (Compound 38)

The same procedures as in Example 29 were carried out except for the use of 2-chloro-5-trifluoromethylbenzaldehyde in place of 2,5-difluorobenzaldehyde in the process of Example 29, to recover 7,9-dihydroxy-2-trifluoromethyl-10,11-dihydrodibenz[b,f]oxepin-10-one (Compound 38) represented by the following formula in pale mud yellow needles.

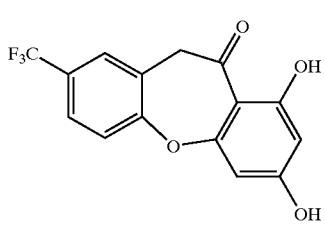

Compound 38

The Compound 38 has a melting point of 172.9 to 174.7° C. By $^1$H-NMR (90 MHz, DMSO-$_6$), the Compound 38 has the peaks shown below.
δ(ppm)
4.25(2H, s, Ar—C$\underline{H_2}$)
6.11(1H, d, J=2.5 Hz, Ar—$\underline{H}$)
6.42(1H, d, J=2.5 Hz, Ar—$\underline{H}$)
7.5–7.9(3H, m, Ar—$\underline{H}$)
12.96(1H, s, O$\underline{H}$)

PRODUCTION EXAMPLE 39

Production of 8-trifluoromethyl-10,11-dihydrodibenz[b,f]oxepin -1,3-diol (Compound 39)

The same procedures as in Example 12 were carried out except for the use of 7,9-dimethoxy-2-trifluoromethyl-10, 11-dihydrodibenz[b,f]oxepin-10-one produced in the step 2 of Example 38 as a starting material in the process of Example 12, to recover 8-trifluoromethyl-10,11-dihydrodibenz[b,f]oxepin-1,3-diol (Compound 39) represented by the following formula in pale pink plates.

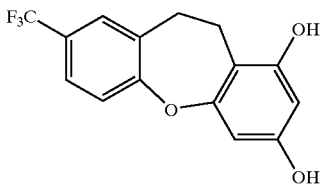

Compound 39

The Compound 39 has a melting point of 177.9 to 179.9° C. By $^1$H-NMR (90 MHz, CDCl$_3$), the Compound 39 has the peaks shown below.

δ(ppm)
2.9–3.0(2H, m, C$\underline{H}_2$)
3.1–3.3(2H, m, C$\underline{H}_2$)
4.6–5.0(1H, br, O$\underline{H}$)
6.11(1H, d, J=2.7 Hz, Ar—$\underline{H}$)
6.32(1H, d, J=2.7 Hz, Ar—$\underline{H}$)
7.1–7.2(1H, m, Ar—$\underline{H}$)
7.4–7.6(2H, m, Ar—$\underline{H}$)

PRODUCTION EXAMPLE 40

Production of 2,3,7,9-tetrahydroxy-10,11-dihydrodibenz[b,f]oxepin-10-one (Compound 40)

The same procedures as in Example 29 were carried out except for the use of 2-bromo-4,5-dimethoxybenzaldehyde in place of 2,5-difluorobenzaldehyde in the process of Example 29, to recover 2,3,7,9-tetrahydroxy-10,11-dihydrodibenz[b,f]oxepin-10-one (Compound 40) represented by the following formula in brown amorphous powder.

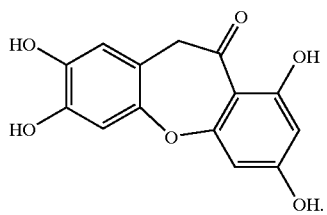

Compound 40

By $^1$H-NMR (90 MHz, DMSO-d$_6$), the Compound 40 has the peaks shown below.

δ(ppm)
3.85(2H, s, Ar—C$\underline{H}_2$)
6.04(1H, d, J=2.3 Hz, Ar—$\underline{H}$)
6.27(1H, d, J=2.3 Hz, Ar—$\underline{H}$)
6.68(1H, s, Ar—$\underline{H}$)
6.68(1H, s, Ar—$\underline{H}$)
9.0–9.3(1H, br, O$\underline{H}$)
12.93(1H, s, O$\underline{H}$)

PRODUCTION EXAMPLE 41

Production of 4-propyl-10,11-dihydrodibenz[b,f]oxepin-1,3-diol (Compound 41)

Triphenylphosphine ethylbromide (4.1 g) was added to 2N sodium hydroxide/dimethyl sulfoxide solution (11 ml), prior to stirring at 50° C. for 30 minutes. To the mixture was added 4,6-dimethoxy-2-hydroxybenzaldehyde (1 g), for stirring at 50° C. overnight. The resulting solution was partitioned between ethyl acetate and dilute hydrochloric acid, and the resulting ethyl acetate phase was washed in water and subsequently in an aqueous saturated sodium chloride solution and dried over anhydrous magnesium sulfate, to distill off the solvents under reduced pressure. The residue was purified by silica gel column chromatography (developing solvent:hexane:ethyl acetate=3:1), followed by addition of a catalytic amount of platinum dioxide for hydrogenation, to recover 3,5-dimethoxy-2-propylphenol (0.5 g; yield of 46%). By $^1$H-NMR (90 MHz, CDCl$_3$), the compound has the peaks shown below.

δ(ppm)
0.94(3H, t, J=7.2 Hz, C$\underline{H}_3$)
1.5–1.8(2H, m, C$\underline{H}_2$)
2.52(2H, t, J=7.5 Hz, Ar—C$\underline{H}_2$)
3.76(3H, s, OC$\underline{H}_3$)
3.77(3H, s, OC$\underline{H}_3$)
6.04(1H, d, J=2.4 Hz, Ar—$\underline{H}$)
6.08(1H, d, J=2.4 Hz, Ar—$\underline{H}$)

The same procedures as in Example 12 were carried out except for the use of the above compound in place of 3,5-dimethoxyphenol in the step 1 of Example 12, to recover 4-propyl-10,11-dihydrodibenz[b,f]oxepin-1,3-diol (Compound 41) represented by the following formula in red oil.

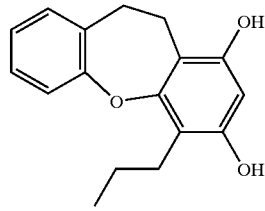

Compound 41

By $^1$H-NMR (90 MHz, CDCl$_3$), the Compound 41 has the peaks shown below.

δ(ppm)
1.03(3H, t, J=7.2 Hz, C$\underline{H}_3$) 1.4–1.8(2H, m, C$\underline{H}_2$)
2.6–2.8(2H, m, C$\underline{H}_2$)
2.9–3.2(2 H, m, C$\underline{H}_2$)
2.9–3.2(2H, m, C$\underline{H}_2$)
4.71(1H, brs, O$\underline{H}$)
6.10(1H, s, Ar—$\underline{H}$)
6.9–7.2(4H, m, Ar—$\underline{H}$)

PRODUCTION EXAMPLE 42

Production of 2-propyl-10,11-dihydrodibenz[b,f]oxepin-1.3-diol (Compound 42)

Anhydrous tetrahydrofuran (36 ml) was added to triphenylphosphine ethyl bromide (12.3 g) prior to stirring at room temperature for 20 minutes. To the resulting mixture was added potassium tert-butoxide (4.5 g), for stirring at room temperature for 30 minutes. Then, 2,6-dimethoxy-4-hydroxybenzaldehyde (3.0 g) was added to the resulting mixture for stirring at room temperature for 2 hours. The resulting solution was partitioned between ethyl acetate and dilute hydrochloric acid, and the resulting ethyl acetate phase was washed in water and subsequently in an aqueous saturated sodium chloride solution and dried over anhydrous magnesium sulfate, to distill off the solvents under reduced pressure. The residue was purified by silica gel column chromatography (developing solvent:hexane:ethyl acetate= 2:1), followed by addition of a catalytic amount of platinum dioxide for hydrogenation, to recover 3,5-dimethoxy-4-propylphenol (1.8 g; yield of 55%). By $^1$H-NMR (90 MHz, CDCl$_3$), the compound has the peaks shown below.

δ(ppm)

0.89(3H, t, J=7.2 Hz, CH$_3$)

1.3–1.6(2H, m, CH$_2$)

2.51(2H, t, J=7.5 Hz, Ar—CH$_2$)

3.75(3H, s, OCH$_3$)

3.75(3H, s, OCH$_3$)

4.71(1H, s, OH)

6.05(1H, s, Ar—H)

6.05(1H, s, Ar—H)

The same procedures as in Example 12 were carried out except for the use of the above compound in place of 3,5-dimethoxyphenol in the step 1 of Example 12, to recover 2-propyl-10,11-dihydrodibenz[b,f]oxepin-1,3-diol (Compound 42) represented by the following formula in yellow needles.

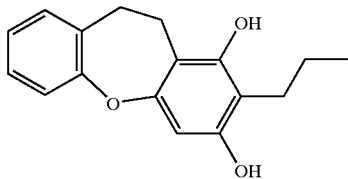

Compound 42

The Compound 42 has a melting point of 109.4 to 111.4° C. By $^1$H-NMR (90 MHz, CDCl$_3$), the Compound 42 has the peaks shown below.

δ(ppm)

0.96(3H, t, J=7.2 Hz, CH$_3$)

1.3–1.7(2H, m, CH$_2$)

2.53(2H, t, J=7.6 Hz, CH$_2$)

2.8–3.3(2H, m, CH$_2$)

2.8–3.3(2H, m, CH$_2$)

4.61(1H, brs, OH) 4.74(1H, brs, OH)

6.32(1H, s, Ar—H)

7.0–7.2(4H, m, Ar—H)

PRODUCTION EXAMPLE 43

Production of 7,8-dihydroxy-10,11-dihydrodibenzo [b,f]thiepin-10-one (Compound 43)

1,2-Dimethoxybenzene (10 g) was dissolved in methylene chloride (50 ml), prior to stirring at 0° C. To the resulting solution was added dropwise chlorosulfonic acid (23.5 ml), for stirring at 45° C. for one hour. The reaction solution was then added dropwise into methanol (150 ml) at 0° C., followed by addition of conc. hydrochloric acid (29 ml) and stannous chloride (57 g), for overnight stirring at room temperature. To the resulting solution after concentration was added 12% hydrochloric acid (125 ml), which was then extracted into toluene three times. The organic phase was washed in water and subsequently in an aqueous saturated sodium chloride solution and dried over anhydrous magnesium sulfate, to distill off the solvents under reduced pressure. The same procedures as in Example 8 were carried out except for the use of the above residue without purification in place of 2,3-dimethoxyphenol in the step 1 of Example 8, to recover 7,8-dihydroxy-10,11-dihydrodibenzo[b,f]thiepin-10-one (Compound 43) represented by the following formula in brown plates.

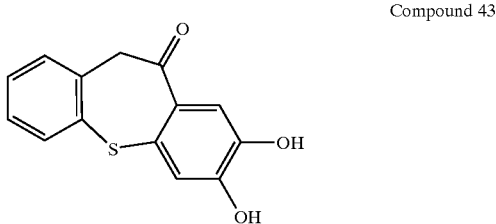

Compound 43

The Compound 43 has a melting point of 247.0 to 248.50° C. By $^1$H-NMR (90 MHz, DMSO-d$_6$), the Compound 43 has the peaks shown below.

δ(ppm)

4.24(2H, s, Ar—CH$_2$)

6.98(1H, s, Ar—H)

7.2–7.8(4H, m, Ar—H)

7.52(1H, s, Ar—H)

PRODUCTION EXAMPLE 44

Production of 10.11-dihydrodibenzo[b,f]thiepin-2,3-diol (Compound 44)

The same procedures as in Example 12 were carried out except for the use of 7,8-dimethoxy-10,11-dihydrodibenzo [b,f]thiepin-10-one produced in the step 2 of Example 43 as a starting mate rial in the process of Example 12, to recover 10,11-dihydrodibenz[b,f]thiepin-2,3-diol (Compound 44) represented by the following formula in pale pink plates.

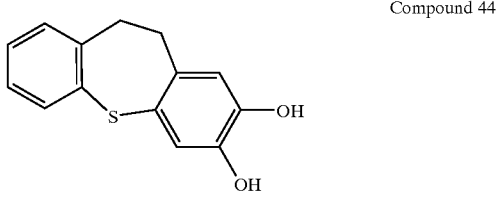

Compound 44

The Compound 44 has a melting point of 116.4 to 118.4° C. By $^1$H-NMR (90 MHz, CDCl$_3$), the Compound 44 has the peaks shown below.

δ(ppm)

3.2–3.4(2H, m, CH$_2$)

3.2–3.4(2H, m, CH$_2$)

6.68(1H, s, Ar—H)

6.98(1H, s, Ar—H)

7.0–7.5(4H, m, Ar—H)

PRODUCTION EXAMPLE 45

Production of (±)-2,3-dihydroxy-10,11-dihydrodibenzo[b,f]thiepin-5-oxide (Compound 45)

10,11-Dihydrodibenzo[b,f]thiepin-2,3-diol (100 mg) produced in Example 44 was dissolved in methylene chloride (1 ml), followed by addition of m-chloroperbenzoic acid (100 mg) for stirring at room temperature for 10 minutes. Diluting the solution with ethyl acetate, washing the solution in water and in an aqueous saturated sodium chloride solution, drying then the resulting solution over anhydrous magnesium sulfate, the solvents were distilled off under reduced pressure. The residue was purified by silica gel column chromatography (developing solvent:hexane:ethyl acetate=1:2) and recrystallized in hot methanol, to recover (±)-2,3-dihydroxy-10,11-dihydrodibenzo[b,f]thiepin-5-oxide (Compound 45) represented by the following formula in mud yellow amorphous powder (90 mg; yield of 38%).

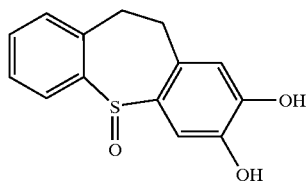

Compound 45

The Compound 45 has a melting point of 218.4 to 219.9° C. By $^1$H-NMR (90 MHz, DMSO-$d_6$), the Compound 45 has the peaks shown below.

δ(ppm)

2.9–3.3(2H, m, C$\underline{H}_2$)

2.9–3.3(2H, m, C$\underline{H}_2$)

6.63(1H, s, Ar—$\underline{H}$)

7.05(1H, s, Ar—$\underline{H}$)

7.3–7.7(4H, m, Ar—$\underline{H}$)

9.24(1H, brs, O$\underline{H}$)

9.34(1H, brs, O$\underline{H}$)

PRODUCTION EXAMPLE 46

Production of 2-acetyl-10,11-dihydrodibenz[b,f]oxepin-1,3-diol (Compound 46)

To anhydrous methylene chloride (0.5 ml) were added aluminium chloride (129 mg) and acetyl chloride (69 μl), and the resulting mixture was stirred at room temperature. After dissolution to the mixture was then added the Compound 12 (0.2 g) produced in Example 12, prior to stirring for another one hour at room temperature. The resulting reaction solution was partitioned between ethyl acetate and dilute hydrochloric acid, and the organic phase was washed in water and in an aqueous saturated sodium chloride solution, and dried over anhydrous magnesium sulfate, to distill off the solvents under reduced pressure. The residue was purified by silica gel column chromatography (developing solvent:ethyl acetate:hexane=1:3) and recrystallized in hexane and ethyl acetate, to recover 2-acetyl-10,11-dihydrodibenz[b,f]oxepin-1,3-diol (Compound 46) represented by the following formula in pale yellow needles (0.05 g; yield of 21%).

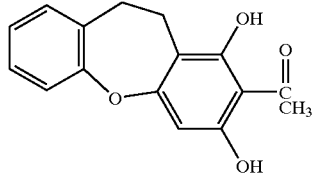

Compound 46

The Compound 46 has a melting point of 146.3 to 147.8° C. By $^1$H-NMR (90 MHz, CDCl$_3$), the Compound 46 has the peaks shown below.

δ(ppm)

2.69(3H, s, C$\underline{H}_3$)

2.8–3.0(2H, m, C$\underline{H}_2$)

3.0–3.2(2H, m, C$\underline{H}_2$)

6.14(1H, s, Ar—$\underline{H}$)

6.4(1H, brs, O$\underline{H}$)

7.0–7.2(4H, m, Ar—$\underline{H}$)

13.5(1H, brs, O$\underline{H}$)

PRODUCTION EXAMPLE 47

Production of 4-acetyl-10,11-dihydrodibenz[b,f]oxepin-1,3-diol (Compound 47)

During the purification process by silica gel column chromatography in Example 46, a compound with a slightly higher polarity than that of the Compound 46 was recrystallized in hexane and ethyl acetate, to recover 4-acetyl-10,11-dihydrodibenz[b,f]oxepin-1,3-diol (Compound 47) represented by the following formula in yellow needles.

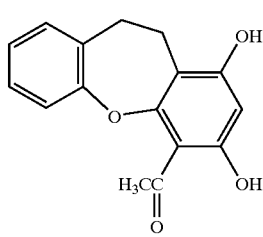

Compound 47

The Compound 47 has a melting point of 169.1 to 170.6° C. By $^1$H-NMR (90 MHz, CDCl$_3$), the Compound 47 has the peaks shown below.

δ(ppm)

2.90(3H, s, C$\underline{H}_3$)

2.9–3.1(2H, m, C$\underline{H}_2$)

3.1–3.3(2H, m, C$\underline{H}_2$)

6.11(1H, s, Ar—$\underline{H}$)

7.1–7.2(4H, m, Ar—$\underline{H}$)

PRODUCTION EXAMPLE 48

Production of 4,8-diacetyl-10,11-dihydrodibenz[b,f]oxepin-1,3-diol (Compound 48).

The same procedures as in Example 46 were carried out except for the use of two-equivalents of the reaction reagents to the Compound 12 in the process of Example 46, to recover 4,8-diacetyl-10,11-dihydrodibenz[b,f]oxepin-1,3-diol (Compound 48) represented by the following formula in pale yellow plates.

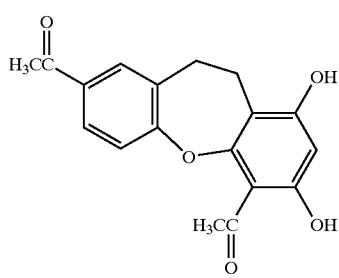

Compound 48

The Compound 48 has a melting point of 220.3 to 222.1° C. By $^1$H-NMR (90 MHz, DMSO-$d_6$), the Compound 48 has the peaks shown below.

δ(ppm)

2.56(3H, s, C$\underline{H}_3$)

2.64(3H, s, C$\underline{H}_3$)

2.7–2.9(2H, m, C$\underline{H}_2$)

3.0–3.2(2H, m, C$\underline{H}_2$)

6.28(1H, s, Ar—$\underline{H}$)

7.26(1H, d, J=8.1 Hz, Ar—$\underline{H}$)

7.7–7.9(2H, m, Ar—$\underline{H}$)

10.9–11.3(1H, br, O$\underline{H}$)

PRODUCTION EXAMPLE 49

Production of 1-fluoro-7,9-dihydroxy-10,11-dihydrodibenz[b,f]oxepin-10-one (Compound 49)

N,N-Dimethylformamide (20 ml) was added to 2-chloro-6-fluorophenyl acetic acid (3.77 g), 3,5-dimethoxyphenol (3.08 g), potassium carbonate (5.52 g), copper iodide (950 mg) and copper (250 mg), for stirring at 120° C. for 20 hours. The resulting solution was partitioned between ethyl acetate and dilute hydrochloric acid, and the organic phase was washed in water and in an aqueous saturated sodium chloride solution, and dried over anhydrous magnesium sulfate, to distill off the solvents under reduced pressure. The residue was purified by silica gel column chromatography (developing solvent:hexane:ethyl acetate=7:3), to recover 2-(3,5-fluorophenyl) acetic acid (5.27 g; yield of 86%). By $^1$H-NMR (90 MHz, CDCl$_3$), the compound has the peaks shown below.

δ(ppm)

3.72(3H, s, OC$\underline{H}_3$)

3.72(3H, s, OC$\underline{H}_3$)

3.75(2 H, s, Ar—C$\underline{H}_2$)

5.8–6.2(3H, m, Ar—$\underline{H}$)

6.5–7.2(3H, m, Ar—$\underline{H}$)

The same procedures as the procedures in and after the step 2 of Example 8 were carried out on the above compound, to recover 1-fluoro-7,9-dihydroxy-10,11-dihydrodibenz[b,f]oxepin-10-one (Compound 49) represented by the following formula in pale yellow needles.

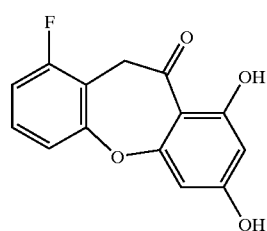

Compound 49

The Compound 49 has a melting point of 217.9 to 219.4° C. By $^1$H-NMR (90 MHz, DMSO-$d_6$), the Compound 49 has the peaks shown below.

δ(ppm)

4.11(2H, s, Ar—C$\underline{H}_2$)

6.18(1H, d, J=2.3 Hz, Ar—$\underline{H}$)

6.39(1H, d, J=2.3 Hz, Ar—$\underline{H}$)

7.2–7.4(3H, m, Ar—$\underline{H}$)

12.88(1H, s, O$\underline{H}$)

PRODUCTION EXAMPLE 50

Production of 9-fluoro-10,11-dihydrodibenz[b,f]oxepin-1,3-diol (Compound 50)

The same procedures as in Example 12 were carried out except for the use of 1-fluoro-7,9-dimethoxy-10,11-dihydrodibenz[b,f]oxepin-10-one produced as an intermediate during the process of producing the Compound 49 in Example 49 as a starting material in the process of Example 12, to recover 9-fluoro-10,11-dihydrodibenz[b,f]oxepin-1,3-diol (Compound 50) represented by the following formula in colorless amorphous powder.

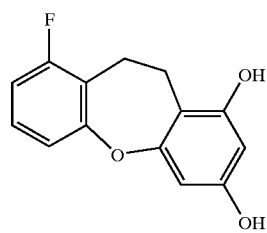

Compound 50

The Compound 50 has a melting point of 184.9 to 186.0° C. By $^1$H-NMR (90 MHz, DMSO-$d_6$), the Compound 50 has the peaks shown below.

δ(ppm)

2.8–3.0(2H, m, C$\underline{H}_2$)

2.8–3.0(2H, m, C$\underline{H}_2$)

6.07(1H, d, J=2.1 Hz, Ar—$\underline{H}$)

6.14(1H, d, J=2.1 Hz, Ar—$\underline{H}$)

6.9–7.3(3H, m, Ar—$\underline{H}$)

9.3–9.5(1H, br, O$\underline{H}$)

9.3–9.5(1H, br, O$\underline{H}$)

PRODUCTION EXAMPLE 51

Production of 1-fluoro-7,8-dihydroxy-10,11-dihydrodibenz[b,f]oxepin-10-one (Compound 51)

The same procedures as in Example 49 were carried out except for the use of 3,4-dimethoxyphenol in place of 3,5-dimethoxyphenol in the process of Example 49, to recover 1-fluoro-7,8-dihydroxy-10,11-dihydrodibenz[b,f]oxepin-10-one (Compound 51) represented by the following formula in skin-colored needles.

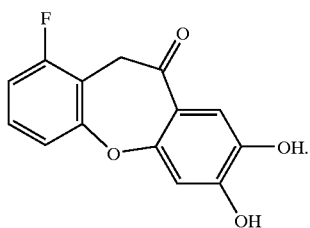

Compound 51

The Compound 51 has a melting point of 215.4 to 217.4° C. By $^1$H-NMR (90 MHz, DMSO-$d_6$), the Compound 51 has the peaks shown below.

δ(ppm)
4.00(2H, s, Ar—C$\underline{H}_2$)
6.80(1H, s, Ar—$\underline{H}$)
7.0–7.4(4H, m, Ar—$\underline{H}$)
9.7–10.1(1H, br, O$\underline{H}$)

PRODUCTION EXAMPLE 52

Production of 9-fluoro-10,11-dihydrodibenz[b,f]oxepin-2,3-diol (Compound 52)

The same procedures as in Example 12 were carried out except for the use of 1-fluoro-7,8-dimethoxy-10,11-dihydrodibenz[b,f]oxepin-10-one produced as an intermediate during the process of producing the Compound 51 in Example 51 as a starting material in the process of Example 12, to recover 9-fluoro-10,11-dihydrodibenz[b,f]oxepin-2,3-diol (Compound 52) represented by the following formula in colorless plates.

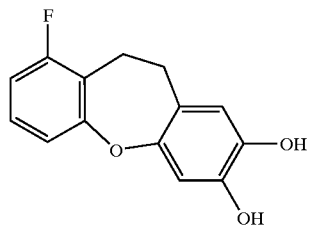

Compound 52

The Compound 52 has a melting point of 121.3 to 123.3° C. By $^1$H-NMR (90 MHz, DMSO-$d_6$), the Compound 52 has the peaks shown below.

(ppm)
2.9–3.0(2H, m, C$\underline{H}_2$)
2.9–3.0(2H, m, C$\underline{H}_2$)
6.56(1H, s, Ar—$\underline{H}$)
6.58(1H, s, Ar—$\underline{H}$)
6.8–7.3(3H, m, Ar—$\underline{H}$)
8.7–9.1(1H, br, O$\underline{H}$)

PRODUCTION EXAMPLE 53

Production of 7-hydroxy-10,11-dihydrodibenz[b,f]oxepin-10-one (Compound 53)

Except for the use of 3-methoxyphenol in place of 2,3-dimethoxyphenol at the first step of the production process of the aforementioned Production Example 8, the same procedures as at the first to third stage of the above Production Example 8 were carried out, to recover the entitled Compound 53 represented by the following formula in a skin-colorplates.

The melting point of the Compound 53 was 188.5–189.3° C.

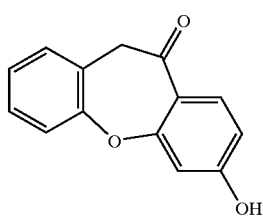

Compound 53

PRODUCTION EXAMPLE 54

Production of 9-hydroxy-7-methoxy-10,11-dihydrodibenz[b,f]oxepin-10-one (Compound 54)

By recrystallizing in ethyl acetate and hexane a compound (Rf value of 0.67) with a lower polarity than that of the Compound 11 at the purification process by silica gel column chromatography (with an elution solvent of ethyl acetate and hexane (3:1)) at the second stage of the production process of the Production Example 11, the entitled Compound 54 represented by the following formula was recovered as colorless plates.

The melting point of the Compound 54 was 119.1–121.1° C.

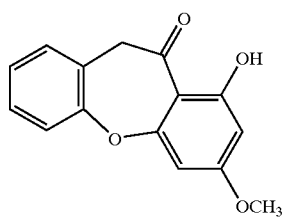

Compound 54

PRODUCTION EXAMPLE 55

Production of 10,11-dihydrodibenz[b,f]oxepin-1,3-diglycolic acid (Compound 55)

N,N-Dimethylformamide (0.6 ml), potassium carbonate (90 mg) and methyl bromoacetate (51 µl) were added to 50 mg of the Compound 12 recovered in the Production Example 12, and the resulting mixture was stirred at room temperature for 2 hours. The reaction solution was pratitioned between ethyl acetate and dilute hydrochloric acid, and the resulting ethyl acetate layer was washed in water and then in an aqueous saturated sodium chloride solution and dried over anhydrous magnesium sulfate, followed by distilling off the solvent under reduced pressure. To the residue were added individually 0.5 ml of methanol and 0.5 ml of an aqueous 10% sodium hydroxide solution, for stirring at room temperature for one hour. The resulting solution was added dropwise to dilute hydrochloric acid, followed by stirring at room temperature for one hour, to recover the entitled Compound 55 (50 mg) represented by the following formula (56) as colorless amorphous powder (yield of 66%). The melting point of the Compound 55 was 212.3–217.4° C.

Compound 55

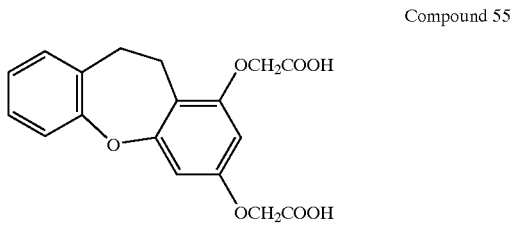

PRODUCTION EXAMPLE 56

Production of 1,3-bis(2-hydroxyethoxy)-10,11-dihydrodibenz[b,f]oxepin (Compound 56)

N,N-Dimethylformamide (0.6 ml), potassium carbonate (90 mg) and methyl bromoacetate (51 µl) were added to 50 mg of the Compound 12 recovered in the Production Example 12, and the resulting mixture was stirred at room temperature for 2 hours. The reaction solution was partitioned between ethyl acetate and dilute hydrochloric acid, and the resulting ethyl acetate layer was washed in water and then in an aqueous saturated sodium chloride solution and dried over anhydrous magnesium sulfate, followed by distilling off the solvent under reduced pressure. To the residue was added anhydrous diethyl ether of 0.5 ml, for stirring at 0° C. Then, LiAlH$_4$(20 mg) was added to the resulting mixture, followed by stirring at room temperature for 2 hours. To the resulting mixture were added trace amounts of ethyl acetate and an aqueous saturated sodium chloride solution, followed by filtration and evaporation of the solvent under reduced pressure. The residue was purified by silica gel column chromatography (elution solvent; ethyl acetate:hexane=1:2), followed by recrystallization in ethyl acetate and hexane, to recover the entitled Compound 56(40 mg; yield of 58%) as colorless needles, represented by the following formula. The melting point of the Compound 56 was 111.5–113.5° C.

Compound 56

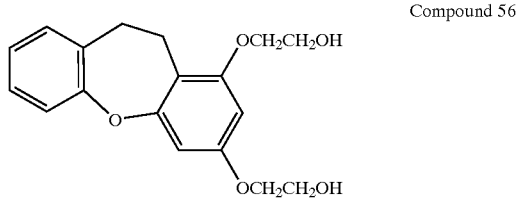

PRODUCTION EXAMPLE 57

Production of 6.7,9-trimethoxy-10,11-dihydrodibenz[b,f]oxepin-10-one (Compound 57)

N,N-Dimethylformamide (50 ml), potassium carbonate (3.0 g) and methyl iodide (1.1 ml) were added to 2.0 g of the compound recovered at the fourth stage of the Production Example 1, and the resulting mixture was stirred at 50° C. for 4 hours. The reaction solution was partitioned between ethyl acetate and dilute hydrochloric acid, and the resulting ethyl acetate layer was washed in water and then in an aqueous saturated sodium chloride solution and dried over anhydrous magnesium sulfate, followed by distilling off the solvent under reduced pressure. The residue was purified by silica gel column chromatography (elution solvent; ethyl acetate:hexane=1:2), to recover 1-(2-allylphenoxy)-2,3,5-trimethoxybenzene (2.2 g; yield of 100%). The peaks of the compound by $^1$H-NMR (90 MHz, CDCl$_3$) are as follows.

δ(ppm)
3.48(2H, d, J=6.6 Hz, Ar—C$\underline{H}_2$)
3.67(3H, s, OCH$_3$)
3.77(3H, s, OC$\underline{H}_3$)
3.87(3H, s, OC$\underline{H}_3$)
4.9–5.2(2H, m, —C$\underline{H}_2$)
5.8–6.2(1H, m, —C$\underline{H}$=CH$_2$)
5.99(1H, d, J=2.9 Hz, Ar—$\underline{H}$)
6.28(1H, d, J=2.9 Hz, Ar—$\underline{H}$)
6.7–7.3(4H, m, Ar—$\underline{H}$)

By carrying out the same procedures as at the sixth and seventh stages of the Production Example 1 over the compound, the entitled Compound 57 represented by the following formula was recovered as pale yellow plates. The melting point of the Compound 57 was 137.1–138.9° C.

Compound 57

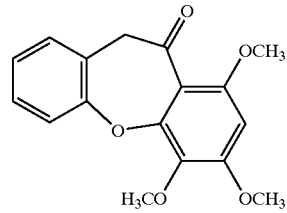

PRODUCTION EXAMPLE 58

Production of 7-methoxy-6,9,10-triacetoxydibenz[b,f]oxepin (Compound 58)

1.25 g of the Compound 1 recovered in the Production Example 1 was dissolved in 15 ml of pyridine (15 ml), followed by addition of acetic anhydride (10 ml), and the resulting mixture was stirred at room temperature for one hour. The reaction solution was diluted with ethyl acetate (200 ml), washed in dilute hydrochloric acid, water and an aqueous saturated sodium chloride solution, and dried over anhydrous magnesium sulfate, followed by evaporation of the solvent under reduced pressure. The residue was purified by silica gel column chromatography (elution solvent; ethyl acetate:hexane=1:1) and recrystallized in ethyl acetate and hexane, to recover the entitled Compound 58 (1.83 g; yield of 100%) represented by the following formula as colorless needles. The melting point of the Compound 58 was 195.6–197.6° C.

Compound 58

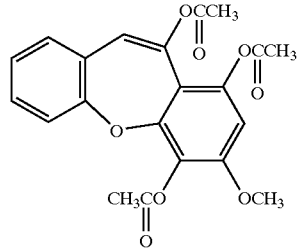

PRODUCTION EXAMPLE 59

Production of 6-acetoxy-9-hydroxy-7-methoxy-10,11-dihydrodibenz[b,f]oxepin-10-one (Compound 59)

100 mg of the Compound 58 recovered in the Production Example 58 was dissolved in 1 ml of methanol, followed by addition of saturated sodium hydrogen carbonate solution (0.5 ml) under heating for dissolution, and the resulting solution was stirred at room temperature for 30 minutes. The reaction solution was diluted with ethyl acetate (10 ml), washed in dilute hydrochloric acid, water and saturated sodium chloride solution, and dried over anhydrous magnesium sulfate, followed by evaporation of the solvent under reduced pressure. The residue was purified by silica gel column chromatography (elution solvent; ethyl acetate:hexane=1:1) and recrystallized in ethyl acetate and hexane, to recover the entitled Compound 59 (30 mg; yield of 40%) represented by the following formula. The peaks of the Compound 59 by $^1$H-NMR (90 MHz, CDCl$_3$) are as shown below.

δ(ppm)

2.46(3H, s, OC$\underline{H}_3$)

3.86(3H, s, OC$\underline{H}_3$)

4.08(2H, s, Ar—C$\underline{H}_2$)

6.29(1H, s, Ar—$\underline{H}$)

7.1–7.4(4H, m, Ar—$\underline{H}$)

13.00(1H, s, O$\underline{H}$)

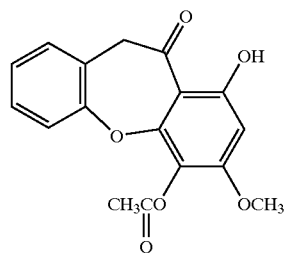

Compound 59

PRODUCTION EXAMPLE 60

Production of 6,7,9,10-tetramethoxydibenz[b,f]oxepin (Compound 60)

70 mg of the Compound 57 recovered in the Production Example 57 was dissolved in methanol (2 ml), followed by addition of ortho-methyl formate (0.6 ml) and para-toluenesulfonic acid (10 mg) and subsequent heating for dissolution, and the resulting solution was stirred at room temperature for 20 minutes. The reaction solution was diluted with ethyl acetate (10 ml), washed in water and an aqueous saturated sodium chloride solution, and dried over anhydrous magnesium sulfate, followed by evaporation of the solvent under reduced pressure. The residue was purified by silica gel column chromatography (elution solvent; ethyl acetate:hexane=2:1), to recover the entitled Compound 60 (70 mg; yield of 95%) represented by the following formula. The peaks of the Compound 60 by $^1$H-NMR (90 MHz, CDCl$_3$) are as shown below.

δ(ppm)

3.78(3H, s, OC$\underline{H}_3$)

3.86(3H, s, OC$\underline{H}_3$)

3.86(3H, s, OC$\underline{H}_3$)

3.98(3H, s, OC$\underline{H}_3$)

6.03(1H, s, Ar—C$\underline{H}$)

6.34(1H, s, Ar—$\underline{H}$)

7.1–7.3(4H, m, Ar—$\underline{H}$)

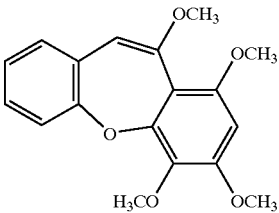

Compound 60

PRODUCTION EXAMPLE 61

Production of 2-fluoro-8-hydroxy-7-methoxy-10,11-dihydrodibenz[b,f]oxepin-10-one (Compound 61)

By recrystallizing in ethyl acetate and hexane the compound which was produced at the second stage of the production process of the Production Example 31 and has Rf value of 0.46 by silica gel column chromatography with an elution solvent of ethyl acetate and hexane (1:1), the entitled compound 61 represented by the following formula was recovered as colorless needles. The melting point of the Compound 61 was 171.5–172.5° C.

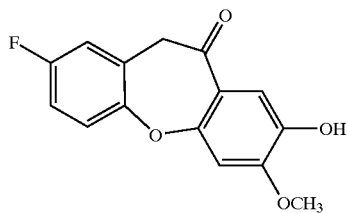

Compound 61

PRODUCTION EXAMPLE 62

Production of 1-fluoro-7,8-dimethoxy-10,11-dihydrodibenz[b,f]oxepin-10-one (Compound 62)

By purifying the compound produced at the second stage of the production process of the Production Example 51 by silica gel column chromatography (elution solvent; methylene chloride) and recrystallizing in ethyl acetate and hexane the resulting purified product, the entitled Compound 62 represented by the following formula was recovered as colorless plates. The melting point of the Compound 62 was 173.3–175.1° C.

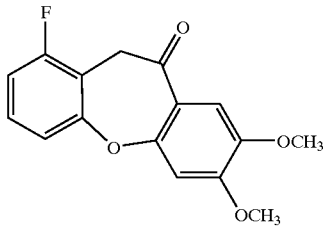

Compound 62

PRODUCTION EXAMPLE 63

Production of 1,7,8-trifluoro-10,11-dihydrodibenz[b,f]oxepin-10-one (Compound 63)

By the same procedures as at the first to second stages of the Production Example 49, except for the use of 3,4- difluorophenol instead of 3,5-dimethoxyphenol at the production process of the Production Example 49, the entitled Compound 63 represented by the following formula was recovered as colorless needles. The melting point of the Compound 63 was 116–117° C.

Compound 63

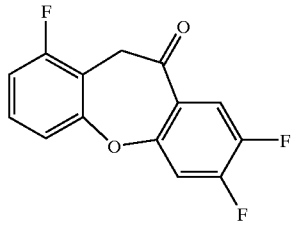

PRODUCTION EXAMPLE 64

Production of 7,8-dimethoxy-10,11-dihydrodibenz[b,f]oxepin-10-one (Compound 64)

By purifying the compound produced at the second stage of the production process of the Production Example 43 by silica gel column chromatography (elution solvent; ethyl acetate:hexane=3:1) and recrystallizing in ethyl acetate and hexane the resulting purified product, the entitled Compound 64 represented by the following formula was recovered as colorless needles. The melting point of the Compound 64 was 162.4–164.4° C.

Compound 64

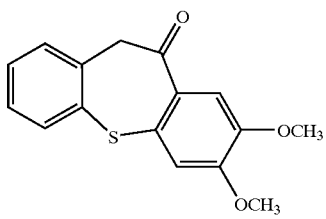

PRODUCTION EXAMPLE 65

Production of 8-hydroxy-7-methoxy-10,11-dihydrodibenzo[b,f]thiepin-10-one (Compound 65)

By recrystallizing in ethyl acetate and hexane the compound which was produced at the second stage of the production process of the Production Example 64 and has Rf value of 0.26 with a higher polarity than that of the Compound 64 at the purification process by silica gel column chromatography with an elution solvent of ethyl acetate and hexane (3:1), the entitled Compound 65 represented by the following formula was recovered as mud-yellow plates. The melting point of the Compound 65 was 219–221° C.

Compound 65

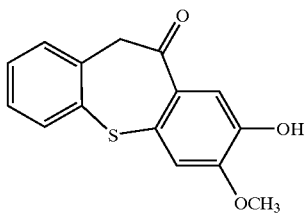

PRODUCTION EXAMPLE 66

Production of 7,8-dihydroxy-10,11-dihydrodibenz[b,f]oxepin-10-one-5,5-dioxide (Compound 66)

100 mg of the Compound 43 recovered in the Production Example 43 was dissolved in 50 ml of methylene chloride, followed by addition of 100 mg of m-chloroperbenzoic acid, and the resulting solution was stirred at room temperature for 30 minutes. The reaction solution was diluted with 100 ml of ethyl acetate, washed in water and saturated sodium chloride solution, and dried over anhydrous magnesium sulfate, prior to evaporation of the solvent under reduced pressure. The residue was purified by silica gel column chromatography (elution solvent; ethyl acetate and hexane= 1:1) and recrystallized in ethyl acetate and hexane, to recover the entitled Compound 66 represented by the following formula as plate yellow amorphous powder (0.07 g; yield of 62%).

The peaks of the Compound 66 by $^1$H-NMR (90 MHz, DMSO-$d_6$) are as follows.

δ(ppm)

4.68(2H, s, Ar—C$\underline{H_2}$)

7.36(1H, s, Ar—$\underline{H}$)

7.44(1H, s, Ar—$\underline{H}$)

7.5–8.1(4H, m, Ar—$\underline{H}$)

10.48(1H, brs, O$\underline{H}$)

10.77(1H, brs, O$\underline{H}$)

The results of the EI-MS analysis of the Compound 66 are as follows. 290(M+), 226(Base).

The results of the FT-IR analysis of the Compound 66 are as follows. 1622 cm$^{-1}$(CO), 1310 cm$^{-1}$(SO$_2$).

Compound 66

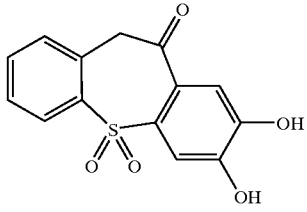

PRODUCTION EXAMPLE 67

Production of 11-bromo-7,8-dihydroxy-10,11-dihydrodibenz[b,f]oxepin-10-one (Compound 67)

150 mg of the Compound 13 recovered in the Production Example 13 was dissolved in 2 ml of THF, followed by addition of 31 μl of bromine at 0° C., and the resulting solution was stirred for one hour. Ethyl acetate was added to the resulting solution, and the organic phase was washed in water and then in an aqueous saturated sodium chloride solution and dried over anhydrous magnesium sulfate, prior to evaporation of the solvent under reduced pressure. The resulting residue was purified by silica gel column chromatography (elution solvent; ethyl acetate and hexane=1:1) and recrystallized in dichloromethane and hexane, to recover the entitled Compound 67 represented by the following formula as skin-colored plates (103 mg). The melting point of the Compound 67 was 178° C. (dec).

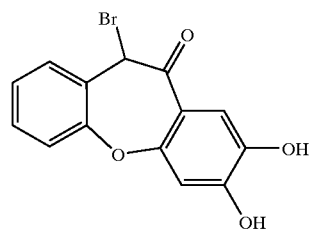

Compound 67

PRODUCTION EXAMPLE 68

Production of 2-fluoro-7-methoxy-10,11-dihydrodibenz[b,f]oxepin-10-on-8-yl trimethane sulfonate (Compound 68)

230 mg of the Compound 61 recovered in the Production Example 61 was dissolved in 2 ml of pyridine, followed by addition of 155 μl of anhydrous triflate at 0° C., and the resulting solution was stirred at room temperature for one hour. Ethyl acetate was added to the resulting solution, and the organic phase was washed in water and then in an aqueous saturated sodium chloride solution and dried over anhydrous magnesium sulfate, prior to evaporation of the solvent under reduced pressure. The resulting residue was purified by silica gel column chromatography (elution solvent; ethyl acetate and hexane=1:4) and recrystallized in dichloromethane and hexane, to recover the entitled Compound 68 represented by the following formula as amorphous yellow crystal (103 mg). The melting point of the Compound 68 was 119–120° C.

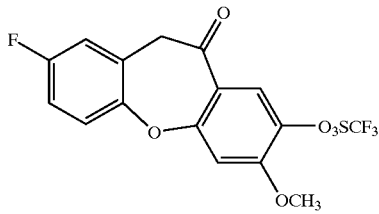

Compound 68

PRODUCTION EXAMPLE 69

Production of 2-fluoro-7-methoxy-8-trimethylsilylethynyl-10,11-dihydrodibenz[b,f]oxepin-10-one (Compound 69)

245 mg of the Compound 68 recovered in the production Example 68, 12.3 mg of triphenylphosphine, 12.2 mg of tris-benzylidene acetone dipalladium chloroform complex, 247 μl of diisopropylethylamine, and 100 μl of ethynyltrimethylsilane were dissolved in 2 ml of N-methyl-2-pyrrolidine, followed by argon substitution, and the resulting solution was heated under stirring at 60° C. for 4 hours. The reaction mixture was diluted with ethyl acetate, washed in water and then an aqueous saturated sodium chloride solution. The organic phase was dried over anhydrous magnesium sulfate, prior to evaporation of the solvent under reduced pressure. The resulting residue was purified by silica gel column chromatography (elution solvent; ethyl acetate and hexane=1:5) and recrystallized in diisopropyl ether and hexane, to recover the entitled Compound 69 represented by the following formula as pale yellow plates (165 mg). The melting point of the Compound 69 was 204–206° C.

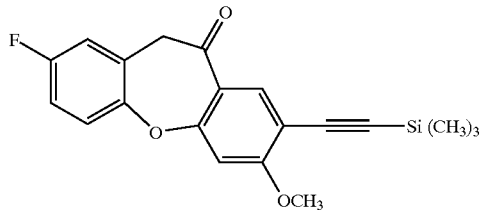

Compound 69

PRODUCTION EXAMPLE 70

Production of 2-nitro-7,9-dihydroxy-10,11-dihydrodibenz[b,f]oxepin-10-one (Compound 70)

First Stage

2-Chloro-5-nitrobenzaldehyde (5.57 g), 3,5-dimethoxyphenol (4.62 g), potassium carbonate (8.29 g), copper powder (0.2 g), copper (I) iodide (0.6 g) and N-methyl-2-pyrrolidone (60 ml) were mixed together and then stirred under heating at 120° C. for 30 minutes. After cooling the reaction mixture to room temperature, the reaction mixture was filtered. The filtrate was diluted with water and extracted with ethyl acetate. The exacted solution was sequentially washed in water and then an aqueous saturated sodium chloride solution, and dried over anhydrous sodium sulfate. The residue after filtration and concentration was purified by silica gel column chromatography (elution solvent; hexane:ethyl acetate=8:2 to 6:4), to recover 2-(3,5-dimethoxyphenoxy)-5-nitrobenzaldehyde (6.54 g; yield of 72%).

The peaks by $^1$H-NMR (90 MHz, CDCl$_3$) are as follows.

δ(ppm)

10.54(d, 1H, J=2 Hz)

8.73(dd, 1H, J=3, 2 Hz)

8.37(ddd, 1H, J=9, 2, 2 Hz)

7.00(dd, 1H, J=9, 2 Hz)

6.41(dd, 1H, J=2, 2 Hz)

6.33(m, 2H)

3.80(s, 6H)

Second Stage

The 2-(3,5-dimethoxyphenoxy)-5-nitrobenzaldehyde (5.64 g) recovered at the first stage was dissolved in a mixture solvent of ethanol (70 ml) and THF (70 ml), followed by addition of sodium borohydride (1.40 g) at 0° C. After stirring at 0° C. for 30 minutes, saturated ammonium chloride solution was added to the resulting mixture to quench the reaction. The reaction solution was concentrated under reduced pressure, followed by addition of hydrochloric acid and extraction with ethyl acetate. The extracted solution was sequentially washed in water and then an aqueous saturated sodium chloride solution, and dried over anhydrous sodium sulfate. The residue recovered by filtration and concentration was dissolved in dichloromethane (140 ml), followed by addition of triphenylphosphine (5.86 g) and carbon tetrabromide (9.26 g). After stirring at room temperature for 5 minutes and addition of saturated sodium hydrogen carbonate solution, the reaction was quenched. The aqueous phase was extracted in dichloromethane, and the resulting exacted solution was washed with an aqueous saturated sodium chloride solution, and dried over anhydrous sodium sulfate. The residue after filtration and concentration was purified by silica gel column chromatography (elution solvent; hexane:ethyl acetate=8:2 to 5:5), to recover 2-(3,5-dimethoxyphenoxy)-5-nitrobenzyl bromide (4.49 g; yield of 66%). The compound was with LRMS (El, 70 eV)m/z of 367, 369($M^+$).

Third Stage

The 2-(3,5-dimethoxyphenoxy)-5-nitrobenzyl bromide (3.25 g) produced at the second stage was dissolved in dichloromethane (120 ml), followed by addition of tetraethylammonium cyanide (1.65 g). After stirring at 40° C. for 1.5 hours, the resulting solution was cooled to room temperature. A The resulting mixture was sequentially washed in water and then an aqueous saturated sodium chloride solution, and dried over anhydrous sodium sulfate. The residue recovered by filtration and concentration was purified by silica gel column chromatography (elution solvent; hexane:ethyl acetate=7:3 to 6:4), to recover 2-(3,5-dimethoxyphenoxy)-5-nitrobenzyl cyanide (2.28 g; yield of 66%). The peaks by $^1$H-NMR (90 MHz, $CDCl_3$) are as follows.

δ(ppm)
8.39(d, 1H, J=3 Hz)
8.15(dd, 1H, J=9, 3 Hz)
6.92(d, 1H, J=9 Hz )
6.38(dd, 1H, J=2, 2 Hz)
6.23(d, 1H, J=2 Hz)
3.89(s, 2H)
3.79(s, 6H)

Fourth Stage

The 2-(3,5-dimethoxyphenoxy)-5-nitrobenzyl cyanide (2.28 g) recovered at the third stage was suspended in acetic acid (22 ml), followed by addition of conc. hydrochloric acid (20 ml). The resulting mixture was heated at 130° C. for 2 hours, and then left to stand at room temperature. The crystals were filtered and washed in water, followed by drying. Then, to the resulting crystal was added polyphosphoric acid (65 ml), and the resulting mixture was heated at 130° C. for 20 minutes. The reaction mixture was poured into water and extracted in ethyl acetate. The extracted solution was sequentially washed in water, an aqueous saturated sodium hydrogen carbonate solution and an aqueous saturated sodium chloride solution, and dried over anhydrous sodium sulfate. After filtration and concentration, 2-nitro-7,9-dimethoxy-10,11-dihydrodibenz[b,f]oxepin-10-one (1.50 g; yield of 66%) was recovered. The peaks by $^1$H-NMR (90 MHz, $CDCl_3$) are as follows.

δ(ppm)
8.13(d, 1H, J=3 Hz )
8.09(dd, 1H, J=9, 3 Hz)
7.30(d, 1H, J=9 Hz)
6.46(d, 1H, J=2 Hz)
6.2 6(d, 1H, J=2 Hz)
4.03(s, 2H)
3.87(s, 3H)
3.80(s, 3H)

Fifth Stage

Pyridine hydrochloride salt (7.5 g) was added to the 2-nitro-7,9-dimethoxy-10,11-dihydrodibenz[b,f]oxepin-10-one (0.31 g) for heating at 190° C. for 2 hours. After cooling the resulting mixture to room temperature, 2N hydrochloric acid was added to the mixture, followed by extraction with ethyl acetate. The extracted solution was washed in an aqueous saturated sodium chloride solution, and dried over anhydrous sodium sulfate. After filtration and concentration, the residue was purified by silica gel column chromatography (elution solvent; hexane:ethyl acetate=6:4). By recrystallizing the purified product in hexane and ethyl acetate, the entitled Compound 70 represented by the formula was recovered as pale yellow needles (0.19 g; yield of 70%). The melting point of the Compound 70 was 193–196° C.

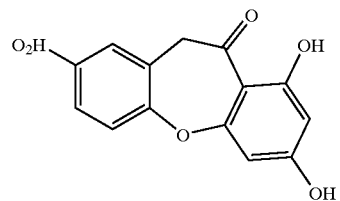

Compound 70

PRODUCTION EXAMPLE 71

Production of 2-amino-7,9-dihydroxy-10,11-dihydrodibenz[b,f]oxepin-10-one (Compound 71)

1.40 g of 2-nitro-7,9-dihydroxy-10,11-dihydrodibenz[b,f]oxepin-10,11 -one (Compound 70) and 4.40 g of tin (II) chloride.$2H_2O$ were suspended in 20 ml of ethanol and 20 ml of 1,4-dioxane, followed by reflux under heating for 3 hours. Water was added to the reaction solution, which was then extracted in ethyl acetate. The extracted solution was sequentially washed in water and then an aqueous saturated sodium chloride solution, and dried over anhydrous sodium sulfate. After filtration and concentration, the residue was purified by silica gel column chromatography (elution solvent; dichloromethane:methanol=95:5), to recover the entitled Compound 71 represented by the formula (0.64 g; yield of 51%). The melting point of the amorphous powder recovered by recrystallization in hexane and ethyl acetate was 227–229° C.

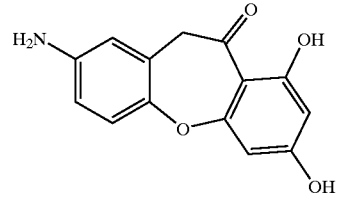

Compound 71

PRODUCTION EXAMPLE 72

Production of 1,7,9-trifluoro-10,11-dihydrodibenz[b,f]oxepin-10-one (Compound 72)

In the same manner as at the first and second stages of the Production Example 49, except for the use of 3,5-difluorophenol instead of 3,5-dimethoxyphenol at the production process of the Production Example 49, the entitled Compound 72 represented by the following formula was recovered as colorless needles. The melting point of the Compound 72 was 114–116° C.

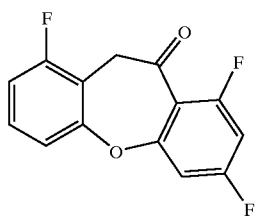

Compound 72

PRODUCTION EXAMPLE 73

Production of 1,7,9-trifluoro-10,11-dihydro-10-hydroxydibenz[b,f]oxepin (Compound 73)

In the same manner as at the first stage of the Production Example 12, except for the use of the Compound 72 produced in the Production Example 72 at the production process of the Production Example 12, the entitled Compound 73 represented by the following formula (was recovered as a colorless amorphous powder. The melting point of the Compound 73 was 104–106° C.

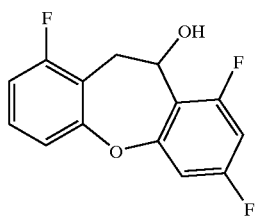

Compound 73

PRODUCTION EXAMPLE 74

Production of 1,3,9-trifluoro-dibenz[b,f]oxepin-10-one (Compound 74)

In the same manner as at the first and second stages of the Production Example 12, except for the use of the Compound 72 produced at the production process of the Production Example 72, the entitled Compound 74 represented by the following formula was recovered as colorless plates. The melting point of the Compound 74 was 101–102° C.

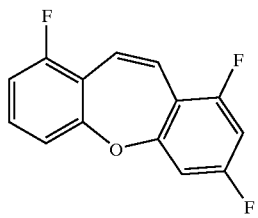

Compound 74

PRODUCTION EXAMPLE 75

Production of 1,3,9-trifluoro-10,11-dihydrodibenz[b,f]oxepin (Compound 75)

In the same manner as in the first stage through the third stage of Production Example 12 except for the use of the Compound 72 produced in the Production Example 72, the title Compound 75 represented by the following formula was prepared as colorless plates. The melting point of this Compound 75 was 33–34° C.

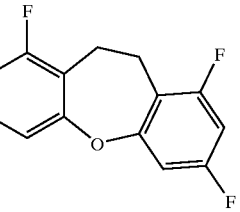

Compound 75

PRODUCTION EXAMPLE 76

Synthesis of 2-propionyl-10,11-dihydrodibenz[b,f]oxepin-1,3-diol (Compound 76)

In the same manner as in the Production Example 46 except for the use of propionyl chloride instead of acetyl chloride, the title Compound 76 represented by the following formula was prepared as yellow needles. The melting point of this Compound 76 was 121.6–123.6° C.

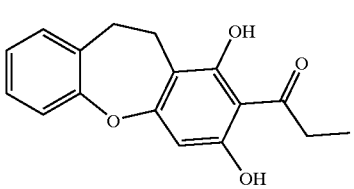

Compound 76

PRODUCTION EXAMPLE 77

Synthesis of 8-amino-10,11-dihydrodibenz[b,f]oxepin-1,3-diol (Compound 77)

In the same manner as in the first stage through the third stage of Production Example 12 except for the use of the compound produced in the fourth stage of the Production Example 70, the title Compound 77 represented by the following formula was prepared. The melting point of this Compound 77 was 176–179° C.

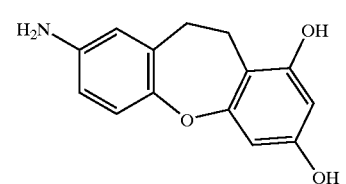

Compound 77

PRODUCTION EXAMPLE 78

Synthesis of 7,8-dihydroxy-2-nitro-10,11-dihydrodibenz[b,f]oxepin-10-one (Compound 78)

In the same manner as in the first stage through the fifth stage of Production Example 70 except for the use of 3,4-dimethoxyphenol instead of 3,5-dimethoxyphenol, the title Compound 78 represented by the following formula was prepared. The melting point of this Compound 78 was 238–242° C.

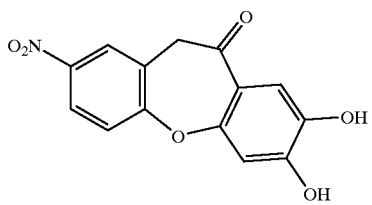

Compound 78

PRODUCTION EXAMPLE 79

Synthesis of 9-hydroxy-7-methoxy-10,11-dihydrodibenzo[b,f]thiepin-10-one (Compound 79)

First Stage

Thiosalicylic acid (44 g), 5-chloro-1,3-dimethoxybenzene (49.2 g), potassium carbonate (78 g), copper (4.3 g) and copper iodide (4.3 g) were dissolved in N-methyl-2-pyrrolidone (390 ml) and the solution was stirred at 190° C. for ten hours. The reaction solution was partitioned between ethyl acetate and diluted hydrochloride and filtered, the organic layer was washed with diluted hydrochloride, water and saturated sodium chloride solution and dried over anhydrous magnesium sulfate and the solvent was evaporated in vacuo. To the residue was added anhydrous tetrahydrofuran (200 ml) and the mixture was dropped into a suspension of lithium aluminum hydride (16.24 g) in anhydrous tetrahydrofuran (100 ml) at 0° C. The reaction solution was stirred overnight at room temperature, saturated sodium chloride solution was added to the reaction solution until no more hydrogen was generated, after decantation the organic layer was evaporated in vacuo. The residue was purified by a silica gel column chromatography (developing solvent; hexane-:ethyl acetate=3:1) to give 2-(3,5-dimethoxyphenylthio) benzyl alcohol (7.9 g; yield of 10%).

The peaks of this compound by $^1$H-NMR (90 MHz, CDCl$_3$) were as follows.

δ(ppm)
3.71(3H, s, OCH$_3$)
3.71(3H, s, OC$\underline{H_3}$)
4.78(2H, s, Ar—C$\underline{H_2}$)
6.2–6.5(3H, m, Ar—$\underline{H}$)
7.3–7.5(4H, m, Ar—$\underline{H}$)

Second Stage 2-(3,5-Dimethoxyphenylthio)benzyl alcohol (7.9 g) was dissolved in methylene chloride (40 ml), then triphenylphosphine (11.2 g) and carbon tetrabromide (11.2 g) were added thereto, the mixture was stirred at room temperature for ten minutes, diluted with ethyl acetate, washed with saturated sodium bicarbonate solution, water and saturated sodium chloride solution and dried over anhydrous magnesium sulfate, and the solvent was evaporated in vacuo. The residue was purified by a silica gel column chromatography (developing solvent; hexane:ethyl acetate=3:1) to give 2-(3,5-dimethoxyphenylthio)-benzyl bromide (9.53 g, yield of 98%).

The peaks of this compound by $^1$H-NMR (90 MHz, CDCl$_3$, δ(ppm)) were as follows.

3.73(3H, s, OCH$_3$)
3.73(3H, s, OC$\underline{H_3}$)
4.70(2H, s, Ar—C$\underline{H_2}$)
6.3–6.4(3H, m, Ar—$\underline{H}$)
7.2–7.5(4H, m, Ar—$\underline{H}$)

Third Stage 2-(3,5-Dimethoxyphenylthio)benzyl bromide (9.53 g) was dissolved in dimethyl sulfoxide (90 ml), sodium cyanide (2.77 g) was added thereto and the mixture was stirred at 80° C. for 1.5 hours. The reaction solution was diluted with ethyl acetate, washed with water and saturated sodium chloride solution and dried over anhydrous magnesium sulfate and the solvent was evaporated in vacuo. The residue was purified by a silica gel column chromatography (developing solvent; hexane:ethyl acetate=3:1) to give 2-(3, 5-dimethoxyphenylthio)-benzyl cyanide (4.91 g, yield of 61%).

The peaks of this compound by $^1$H-NMR (90 MHz, CDCl$_3$, δ(ppm)) were as follows.

3.72(3H, s, OCH$_3$)
3.72(3H, s, OC$\underline{H_3}$)
3.87(2H, s, Ar—C$\underline{H_2}$)
6.2–6.5(3H, m, Ar—$\underline{H}$)
7.3–7.7(4H, m, Ar—$\underline{H}$)

Fourth Stage

To 2-(3,5-dimethoxyphenylthio)benzyl cyanide (4.9 g) were added concentrated hydrochloric acid (26 ml) and concentrated acetic acid (26 ml) followed by stirring at 120° C. for four hours. The reaction solution was diluted with ethyl acetate, washed with water and saturated sodium chloride solution and dried over anhydrous magnesium sulfate, and the solvent was evaporated in vacuo. To the residue was added methanesulfonic acid (26 ml) followed by stirring at room temperature for two nights. The reaction solution was diluted with ethyl acetate, washed with water and saturated sodium chloride solution and dried over anhydrous magnesium sulfate, and the solvent was evaporated in vacuo. The residue was purified by a silica gel column chromatography (developing solvent; hexane:ethyl acetate=3:1) to give 4.1 g (yield of 88%) of the title Compound 79 represented by the following formula as pale yellow needles. The melting point of the Compound 79 was 134.5–136° C.

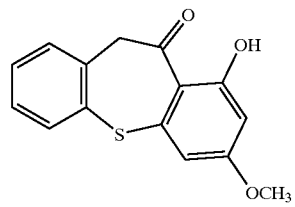

Compound 79

PRODUCTION EXAMPLE 80

Synthesis of 7,9-dihydroxy-10,11-dihydrodibenzo[b, f]thiepin-10-one (Compound 80)

In the same manner as in Production Example 8 except for the use of the Compound 79 prepared in Production Example 79 to give the title Compound 80 represented by the following formula as ocherous plates. The melting point of this Compound 80 was 248.1–250.0° C.

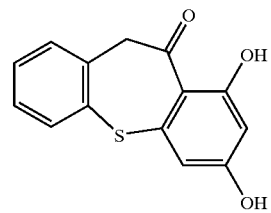

Compound 80

PRODUCTION EXAMPLE 81

Synthesis of 10,11-dihydrodibenzo[b,f]thiepin-1,3-diol (Compound 81)

In the same manner as in the first to third stages of Production Example 12 except for the use of the Compound 79 obtained in Production Example 79, the title Compound 81 in pale skin-colored needles represented by the following formula was prepared. The melting point of this Compound 81 was 167.0–169.2° C.

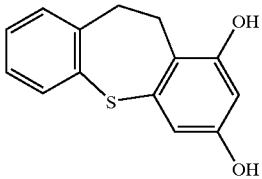

Compound 81

PRODUCTION EXAMPLE 82

Synthesis of 2-acetyl-10,11-dihydrodibenzo[b,f]thiepin-1,3-diol (Compound 82)

In the same manner as in Production Example 46 except for the use of the Compound 81 obtained in Production Example 81 instead of the Compound 12, the title Compound 82 represented by the following formula was prepared as yellow needles. The melting point of this Compound 82 was 181.5–183.2° C.

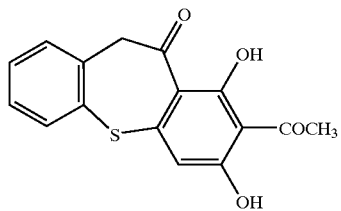

Compound 82

PRODUCTION EXAMPLE 83

Synthesis of 7,9,10-triacetoxydibenzo[b,f]thiepin-1,3-diol (Compound 83)

In the same manner as in Production Example 58 except for the use of the Compound 80 prepared in Production Example 80 instead of the Compound 1, the title Compound 83 represented by the following formula was prepared as colorless needles. The melting point of this Compound 83 was 154.5–156.2° C.

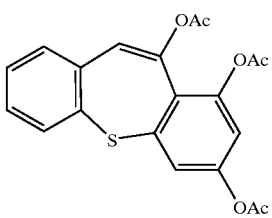

Compound 83

PRODUCTION EXAMPLE 84

Synthesis of 2,4-diacetyl-10,11-dihydrodibenzo[b,f]thiepin-1,3-diol (Compound 84)

In the purifying stage by a silica gel column chromatography in the production steps of Production Example 82, a compound having an Rf value of 0.78 when the developing solvent was ethyl acetate:hexane=3:1 was purified to give pale yellow needles of the title Compound 84 represented by the following formula. The melting point of this Compound 84 was 198.6–200.3° C.

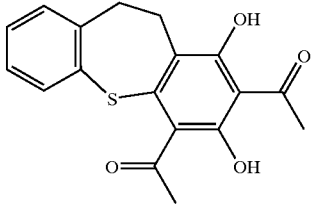

Compound 84

PRODUCTION EXAMPLE 85

Synthesis of 4-acetyl-10,11-dihydrodibenzo[b,f]thiepin-1,3-diol (Compound 85)

In the purifying stage by a silica gel column chromatography in the production steps of Production Example 82, a compound having an Rf value of 0.33 when the developing solvent was ethyl acetate:hexane=3:1 was purified to give ocherous needles of the title Compound 85 represented by the following formula. The melting point of this Compound 85 was 198.6–200.3° C.

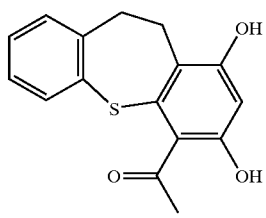

Compound 85

PRODUCTION EXAMPLE 86

Synthesis of 8-acetyl-10,11-dihydrodibenzo[b,f]thiepin-1,3-diol (Compound 86)

In the purifying stage by a silica gel column chromatography in the production steps of Production Example 82, a compound having an Rf value of 0.33 when the developing solvent was ethyl acetate:hexane=3:1 was purified to give the title Compound 86 represented by the following formula. The peaks of this Compound 86 in $^1$H-NMR (400 MHz, CDCl$_3$, δ(ppm)) were as follows.

2.53(3H, s, C$\underline{H}_3$)

2.98–3.01(2H, m, C$\underline{H}_2$)

3.24–3.27(2H, m, C$\underline{H}_2$)

6.25(1H, d, J=2.3 Hz, Ar—$\underline{H}$)

6.30(1H, d, J=2.3 Hz Ar—$\underline{H}$)

7.50(1H, d, J=8.1 Hz, Ar—$\underline{H}$)

7.67(1H, dd, J=8.1, 1.5 Hz, Ar—$\underline{H}$)

7.79(1H, d, J=1.3 Hz, Ar—$\underline{H}$)

9.26(1H, s, O<u>H</u>)

9.51(1H, s, O<u>H</u>)

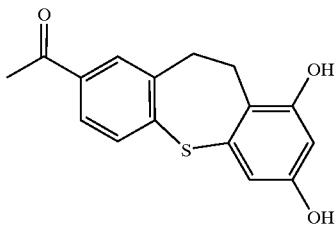
Compound 86

PRODUCTION EXAMPLE 87

Synthesis of 2-propionyl-10,11-dihydrodibenzo[b,f]thiepin-1,3-diol (Compound 87)

In the same manner as in Production Example 46 except for the use of the Compound 81 prepared in Production Example 81 instead of the Compound 12 and also for the use of propionyl chloride instead of acetyl chloride, the title Compound 87 represented by the following formula was prepared as yellow needles. The melting point of this Compound 87 was 140.0–140.4° C.

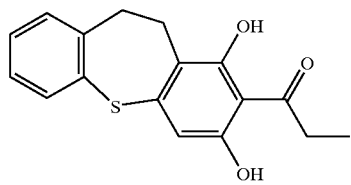
Compound 87

PRODUCTION EXAMPLE 88

Synthesis of 4-propionyl-1-propoxy-10,11-dihydrodibenzo[b,f]thiepin-3ol (Compound 88)

In the purifying stage by a silica gel column chromatography in the production steps of Production Example 87, a compound having an Rf value of 0.34 when the developing solvent was ethyl acetate:hexane=2:1 was purified to give the title Compound 88 represented by the following formula as pale yellow oil. The peaks of this Compound 88 in $^1$H-NMR (400 MHz, CDCl$_3$, δ(ppm)) were as follows.

1.27–1.33(6H, m, C<u>H</u>$_3$)

2.64(2H, q, J=7.5 Hz, C<u>H</u>$_2$)

3.16–3.22(4 H, m, C<u>H</u>$_2$)

3.34–3.37(2H, m, C<u>H</u>$_2$)

6.68(1H, s, Ar—<u>H</u>)

7.08–7.11(2H, m, Ar—<u>H</u>)

7.16–7.20(1H, m, Ar—<u>H</u>)

7.34–7.36(1H, m, Ar—<u>H</u>)

10.20(1H, brs, O<u>H</u>)

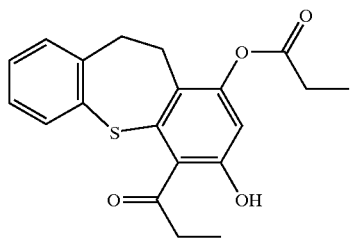
Compound 88

PRODUCTION EXAMPLE 89

Synthesis of 2,4-dipropionyl-10,11-dihydrodibenzo[b,f]thiepin-1,3-diol (Compound 89)

In the purifying stage by a silica gel column chromatography in the production steps of Production Example 87, a compound having an Rf value of 0.91 when the developing solvent was ethyl acetate:hexane=2:1 was purified to give the title compound represented by the following formula. The peaks of this Compound 89 in $^1$H-NMR (400 MHz, CDCl$_3$, δ(ppm)) were as follows.

1.17(3H, t, J=7.1 Hz, C<u>H</u>$_3$)

1.30(3H, t, J=7.3 Hz, C<u>H</u>$_3$)

3.18–3.27(6H, m, C<u>H</u>$_2$)

3.51(2H, d, J=6.6 Hz, C<u>H</u>$_2$)

7.10–7.15(2H, m, Ar—<u>H</u>)

7.18–7.20(1H, m, Ar—<u>H</u>)

7.36(1H, d, J=7.5 Hz, Ar—<u>H</u>)

13.86(1H, s, O<u>H</u>)

14.77(1H, s, O<u>H</u>)

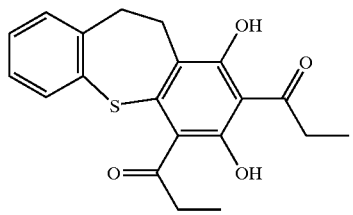
Compound 89

PRODUCTION EXAMPLE 90

Synthesis of 4-propionyl-10,11-dihydrodibenzo[b,f]thiepin-1,3-diol (Compound 90)

In the purifying stage by a silica gel column chromatography in the production steps of Production Example 87, a compound having an Rf value of 0.32 when the developing solvent was ethyl acetate:hexane=2:1 was purified to give the title Compound 90 represented by the following formula. The peaks of this Compound 90 in $^1$H-NMR (400 MHz, CDCl$_3$, δ(ppm)) were as follows.

1.06(3H, t, J=7.2 Hz, C<u>H</u>$_3$)

2.65(2H, q, J=7.2 Hz, C<u>H</u>$_2$)

3.08–3.10(2H, m, C<u>H</u>$_2$)

3.18–3.21(2H, m, C<u>H</u>$_2$)

6.38(1H, s, Ar—H)
7.10–7.12(1H, m, Ar—H)
7.20–7.22(2H, m, Ar—H)
7.27(1H, d, J=7.6 Hz, Ar—H)
9.62(1H, s, OH)
9.73(1H, s, OH)

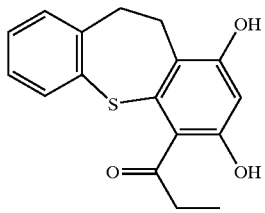

Compound 90

PRODUCTION EXAMPLE 91

Synthesis of 8-propionyl-10,11-dihydrodibenzo[b,f]thiepin-1,3-diol (Compound 91)

In the purifying stage by a silica gel column chromatography in the production steps of Production Example 87, a compound having an Rf value of 0.13 when the developing solvent was ethyl acetate:hexane=2:1 was purified to give the title Compound 91 represented by the following formula. The peaks of this Compound 91 in $^1$H-NMR (400 MHz, CDCl$_3$, δ(ppm)) were as follows.

1.04(3H, t, J=7.1 Hz, CH$_3$)
2.96–3.01(4H, m, CH$_2$)
3.24–3.27(2H, m, CH$_2$)
6.25(1H, d, J=2.3 Hz, Ar—H)
6.30(1H, d, J=2.3 Hz, Ar—H)
7.50(1H, d, J=8.1 Hz, Ar—H)
7.67(1H, d, J=8.1 Hz, Ar—H)
7.79(1H, s, Ar—H)
9.26(1H, s, OH)
9.50(1H, s, OH)

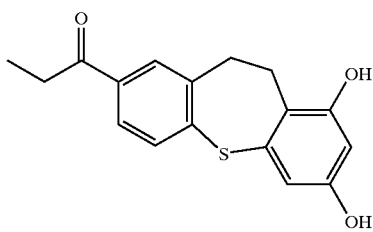

Compound 91

PRODUCTION EXAMPLE 92

Synthesis of 8-acetyldibenzo[b,f]thiepin-2,3-diol (Compound 92)

In the same manner as in Production Example 46 except for the use of the Compound prepared in the second stage of the Production Example 44, the title Compound 92 represented by the following formula was prepared. The peaks of this Compound 92 in $^1$H-NMR (400 MHz, CDCl$_3$, δ(ppm)) were as follows.

2.53(3H, s, CH$_3$)
6.66(1H, s, Ar—H)
6.87(1H, s, Ar—H)
7.36–7.39(2H, m, Ar—H, CH=CH)
7.48–7.54(2H, m, Ar—H, CH=CH)
7.92(1H, s, Ar—H)
9.00–9.50(2H, brs, OH)

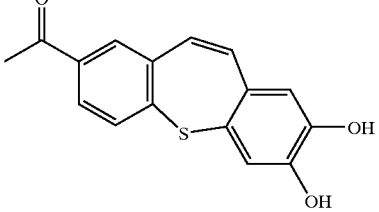

Compound 92

PRODUCTION EXAMPLE 93

Synthesis of N-acetyl-7-acetoxy-2-amino-9-hydroxy-10,11-dihydrodibenzo[b,f]oxepin-10-one (Compound 93)

In the same manner as in Production Example 58 except for the use of the Compound 71 prepared in Production Example 71 and also for the use of sodium bicarbonate and methylene chloride instead of pyridine, the title Compound 93 represented by the following formula was prepared as crystals. The melting point of this Compound 93 was 196–198° C.

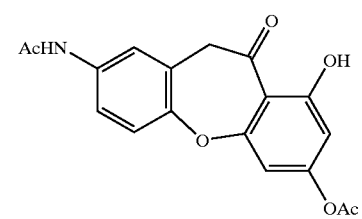

Compound 93

PRODUCTION EXAMPLE 94

Synthesis of N-acetyl-2-amino-7,9-dihydroxy-10,11-dihydrodibenzo[b,f]oxepin-10-one (Compound 94)

In the same manner as in Production Example 59 except for the use of the Compound 93 prepared in Production Example 93, the title Compound 94 represented by the following formula was prepared. The peaks of this Compound 94 in $^1$H-NMR (400 MHz, CDCl$_3$, δ(ppm)) were as follows.

2.01(3H, s)
4.03(2H, s)
6.05(1H, d, J=2 Hz)
6.32(1H, d, J=2 Hz)
7.23(1H, d, J=8 Hz)
7.41(1H, dd, J=8.2 Hz)
7.59(1H, d, J=2 Hz)
9.99(1H, s)

10.97(1H, brs)
12.95(1H, s)

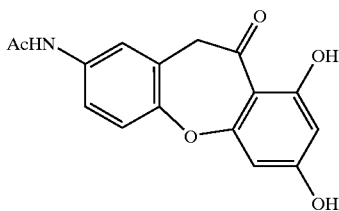

Compound 94

PRODUCTION EXAMPLE 95

Synthesis of 8-acetyl-10,11-dihydrodibenzo[b,f]oxepin-1,3-diol (Compound 95)

First Stage

The Compound 12 (3 g) prepared in Production Example 12 was dissolved in pyridine (50 ml) at room temperature. Acetyl chloride (25 ml) was dropped thereinto at room temperature and the mixture was stirred overnight. The reaction solution was partitioned between ethyl acetate and diluted hydrochloric acid, the organic layer was washed with water and saturated sodium chloride solution and dried over anhydrous magnesium sulfate and the solvent was evaporated in vacuo. The residue was dissolved by adding anhydrous methylene chloride (20 ml) thereto.

Anhydrous methylene chloride (100 ml) was added to aluminum chloride (12 g) and acetyl chloride (10 ml) and the mixture was stirred at room temperature. After dissolution, the mixture was cooled at 0° C. and the above-prepared methylene chloride solution was dropped thereinto at 0° C. After dropping, the mixture was returned to room temperature and stirred overnight. The reaction solution was partitioned between ethyl acetate and diluted hydrochloric acid, the organic layer was washed with water and saturated sodium chloride solution and dried over anhydrous magnesium sulfate and the solvent was evaporated in vacuo. The residue was purified by a silica gel column chromatography (developing solvent; hexane:ethyl acetate=2:1) to give 4.0 g (yield of 97%) of 8-acetyl-1,3-diacetoxy-10,11-dihydrodibenzo[b,f]oxepin as pale yellow oil. The peaks in $^1$H-NMR (400 MHz, CDCl$_3$, δ(ppm)) were as follows.

2.26(3H, s, CH$_3$)
2.30(3H, s, CH$_3$)
2.55(3H, s, CH$_3$)
2.91–3.15(2H, m, CH$_2$)
3.12–3.15(2H, m, CH$_2$)
6.69(1H, d, J=2.3 Hz, Ar—H)
6.92(1H, d, J=2.3 Hz, Ar—H)
7.17(1H, d, J=9.0 Hz, Ar—H)
7.75–7.78(2H, m, Ar—H)

Second Stage

8-Acetyl-1,3-diacetoxy-10,11-dihydrodibenzo[b,f]oxepin (1.5 g) was dissolved in methanol (100 ml). To the solution was added saturated sodium bicarbonate solution (1 ml) and the mixture was stirred for two hours with warming. The reaction was quenched with adding 1N hydrochloric acid to the reaction solution. Methanol was evaporated therefrom in vacuo and the residue was extracted with ethyl acetate. The organic layer was washed with water and saturated sodium chloride solution and dried over anhydrous magnesium sulfate, and the solvent was evaporated in vacuo. The residue was purified by a silica gel column chromatography (developing solvent; hexane:ethyl acetate=1:1). Recrystallization from chloroform-hexane gave 1.2 g (yield of 95%) of colorless plates of the title Compound 95 represented by the following formula. The melting point of the Compound 95 was 209.9–211.9° C.

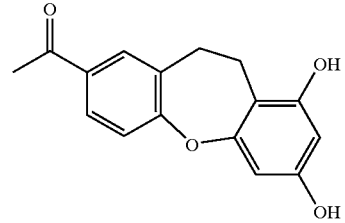

Compound 95

PRODUCTION EXAMPLE 96

Synthesis of 8-(1-hydroxyethyl)-10,11-dihydrodibenzo[b,f]oxepin-1,3-diol (Compound 96)

The Compound 95 (500 mg) prepared in Production Example 95 was dissolved in methanol. The solution was cooled at 0° C. and sodium borohydride (500 mg) was added portionwise. The reaction solution was stirred at room temperature for one hour. The reaction was quenched with adding 1N hydrochloric acid thereto. After evaporating methanol therefrom in vacuo, the residue was extracted with ethyl acetate. The organic layer was washed with water and saturated sodium chloride solution and dried over anhydrous magnesium sulfate, and the solvent was evaporated in vacuo. The residue was purified by a silica gel column chromatography (developing solvent; hexane:ethyl acetate=1:1) to give 180 mg (yield of 36%) of the title Compound 96 represented by the following formula as pale orange-colored oil. The peaks of the Compound 96 in $^1$H-NMR (90 MHz, CDCl$_3$, δ(ppm)) were as follows.

1.42(3H, d, J=6.4 Hz, CH$_3$)
2.9–3.0(2H, m, CH$_2$)
3.0–3.1(2H, m, CH$_2$)
3.22(1H, s, OH)
4.26(1H, q, J=, CH)
4.99(2H, s, Ph—OH)
6.07(1H, d, J=2.4 Hz, Ar—H)
6.31(1H, d, J=2.4 Hz, Ar—H)
7.09(3H, s, Ar—H)

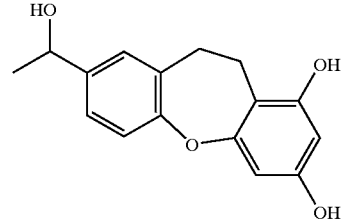

Compound 96

PRODUCTION EXAMPLE 97

Synthesis of 7,9-dihydroxy-10,11-dihydrodibenzo[b,f]oxepin-2-acetic acid (Compound 97)

First Stage

The Compound 95 (800 mg) prepared in Production Example 95 was dissolved in anhydrous acetone (50 ml). To this were added methyl iodide (370 µl) and anhydrous potassium carbonate (400 mg) and the mixture was heated to reflux at 100° C. for three days. The reaction was quenched with adding diluted hydrochloric acid to the reaction solution. Acetone was evaporated in vacuo and the residue was extracted with ethyl acetate. The organic layer was washed with water and saturated sodium chloride solution and dried over anhydrous magnesium sulfate and the solvent was evaporated in vacuo. To the residue were added sulfur (500 mg), morpholine (500 mg) and p-toluenesulfonic acid (100 mg) and the mixture was stirred at 150° C. for five hours. The reaction solution was partitioned between ethyl acetate and diluted hydrochloric acid. The organic layer was washed with water and saturated sodium chloride solution and dried over anhydrous magnesium sulfate, and the solvent was evaporated in vacuo. The residue was purified by a silica gel column chromatography (developing solvent; hexane:ethyl acetate=2:1) to give 400 mg (42% of yield) of a morpholine compound as yellow oil. The peaks of this compound in $^1$H-NMR (90 MHz, CDCl$_3$, δ(ppm)) were as follows.

2.83–3.0(2H, m, CH$_2$)
3.0–3.2(2H, m, CH$_2$)
3.3–3.8(6H, m, CH$_2$×3)
3.76(3H, s, CH$_3$)
3.79(3H, s, CH$_3$)
4.2–4.4(4H, m, CH$_2$×2)
6.21(1H, d, J=2.3 MHz, Ar—H)
6.37(1H, d, J=2.3 MHz, Ar—H)
7.0–7.2(3H, m, Ar—H)

Second Stage

To the morpholine compound (400 mg) were added each 5 ml of concentrated hydrochloric acid and concentrated acetic acid and the mixture was heated to reflux at 150° C. for two hours. Water was added to the reaction solution, the mixture was partitioned between ethyl acetate, the organic layer was washed with water and saturated sodium chloride solution and dried over anhydrous magnesium sulfate and the solvent was evaporated in vacuo. To this was added pyridine hydrochloride (2 g) and the mixture was stirred at 200° C. for four hours. The reaction solution was partitioned between ethyl acetate and diluted hydrochloric acid, the organic layer was washed with water and saturated sodium chloride solution and dried over anhydrous magnesium sulfate and the solvent was evaporated in vacuo. The residue was purified by a silica gel column chromatography (developing solvent; hexane:ethyl acetate=1:1). This was recrystallized from ethyl acetate-hexane to give 163.3 mg (yield of 57%) of the title Compound 97 represented by the following formula as an ocherous amorphous powder. The melting point of this Compound 97 was 222.0–224.0° C.

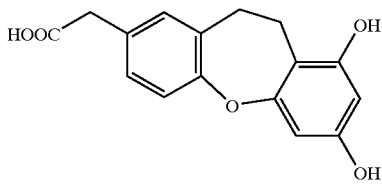

Compound 97

PRODUCTION EXAMPLE 98

Synthesis of 7,8-dihydroxy-10,11-dihydrodibenzo[b,f]oxepin-10-one (Compound 13)

First Stage

Synthesis of 6-bromo-3,4-dimethoxybenzaldehyde

A solution of bromine (0.96 g) in acetic acid (10 ml) was dropped into a solution of 3,4-dimethoxybenzaldehyde (1.0 g) in acetic acid (4 ml) and the mixture was stirred for three hours. Sodium thiosulfate was added to the reaction mixture, then sodium bicarbonate was added thereto and the mixture was filtered. The crude crystals collected by the filtration were recrystallized from chloroform-ether to give the title compound (0.83 g, 56%). The peaks of this compound in $^1$H-NMR (400 MHz, CDCl$_3$) were as follows.

δ3.92(s, 3H), 3.96(s, 3H),
7.05(s, 1H), 7.42(s, 1H),
10.19(s, 1H).

Second Stage

Synthesis of 6-bromo-3,4-dimethoxyacetophenone

A solution of methyl iodide in diethyl ether (1M, 80 ml) diluted with diethyl ether (80 ml) was dropped into a solution of 6-bromo-3,4-dimethoxybenzaldehyde (18 g) in tetrahydrofuran (50 ml) and the mixture was stirred for five minutes. The reaction solution was diluted with ether, saturated ammonium chloride solution was added and the organic layer was collected. The organic layer was washed with water and saturated sodium chloride solution and dried over anhydrous magnesium sulfate. Five grams of the residue obtained after evaporation of the solvent were dissolved in dichloromethane (75 ml) and the solution was stirred for four hours with molecular sieves 4A (10 g) and pyridinium dichromate (10.8 g). The reaction mixture was diluted with ether and filtered off through celite and the solvent was evaporated. The resulting crude crystals were recrystallized from ethyl acetate-hexane to give the title compound (4.4 g, 88%) as reddish orange crystals.

The peaks of this compound in $^1$H-NMR (400 MHz, CDCl$_3$) were as follows.

δ2.67(s, 3H), 3.90(s, 3H),
7.05(s, 1H), 7.14(s, 1H).

Third Stage

Synthesis of 2-(2-bromophenoxy)-4,5-dimethoxyacetophenone

To a solution of 2-bromophenol (380 mg) in N,N-dimethylformamide (2.5 ml) were added potassium carbonate (15 mg), copper (19.5 mg), copper iodide (15 mg) and 6-bromo-3,4-dimethoxyacetophenone (Compound 4) (130 mg) and the mixture was stirred at 100° C. for four hours. The reaction mixture was diluted with ether and 5% aqueous solution of sodium hydroxide was added thereto followed by stirring for five minutes. This was diluted with a mixture of ether and hexane and was washed with 5% aqueous solution of sodium hydroxide, water and saturated sodium chloride solution successively. The organic layer was collected and dried over anhydrous magnesium sulfate and the solvent was evaporated therefrom. The resulting residue was purified by a silica gel chromatography (hexane:ether=3:1) to give the title compound (345 mg, 80%) as yellow oil.

The peaks of this compound in $^1$H-NMR (400 MHz, CDCl$_3$) were as follows.

δ2.61 (s, 3H , 3.79 (s, 3H),
3.94 (s, 3H), 6.37 (s, 1H),
6.78 (dd, 1H, J=2.5, 8.2 Hz),
7.01 (dt, 1H, J=1.5, 8.0 Hz),
7.25 (dt, 1H, J=1.8, 7.2 Hz),
7.50 (s, 1H),
7.66 (dd, 1H, J=1.8, 8.0 Hz),

Fourth Stage

Synthesis of 7,8-dimethoxy-10,11-dihydrobenz[b,f]oxepin-10-one

Liquid ammonia (0.8 ml) and potassium tert-butoxy (20 mg) were added to 2-(2-bromophenoxy)-4,5- dimethoxyacetophenone in an argon atmosphere followed by irradiating with light for 30 minutes. Ether and ammonium chloride were added to the reaction mixture and the ether layer was collected. This was dried over magnesium sulfate and filtered with sodium sulfate. The solvent was evaporated to give the title compound (4 mg, 80%) as white crystals.

The peaks of this compound in $^1$H-NMR (400 MHz, CDCl$_3$) were as follows.

δ3.89(s, 3H), 3.99(s, 3H),
4.06(s, 2H), 6.85(s, 1H),
7.16–7.31(m, 4H),
7.48(s, 1H).

Fifth Stage

Synthesis of 7,8-dihydroxy-10,11-dihydrodibenzo[b,f]oxepin-10-one

A mixture of 7,8-dimethoxy-10,11-dihydrodibenzo[b,f]oxepin-10-one (5 mg) and pyridine hydrochloride (20 mg) was heated at 190° C. for two hours. Water was added to the reaction mixture followed by extracting with ethyl acetate. This was washed with water and dried over magnesium sulfate and the solvent was evaporated to give the title compound (Compound 13) (3 mg, 60%) as brown plates.

The peaks of this compound in $^1$H-NMR (400 MHz, DMSO-d6) were as follows.

δ4.23(s, 2H), 6.97(s, 1H),
7.2–7.5(m, 3H),
7.51(s, 1H),
7.6–7.7(m, 1H),
9.9(br, 2H).

PRODUCTION EXAMPLE 99

Synthesis of 7,8-dihydroxy-2-methyl-10,11-dihydrodibenzo[b,f]oxepin-10-one (Compound 98)

In the same manner as in the first to the fifth stages of Production Example 98 except for the use of 2-bromo-4-cresol instead of 2-bromophenol in the third step of Production Example 98, the title Compound 98 represented by the following formula was prepared. The peaks of this Compound 98 in $^1$H-NMR (400 MHz, DMSO-d6) were as follows.

δ2.25(s, 3H), 4.24(s, 2H),
6.90(d, 1H, J=8 Hz),
6.96(s, 1H), 7.15(brs, 1H),
7.41(d, 1H, J=8 Hz),
7.51(s, 1H).

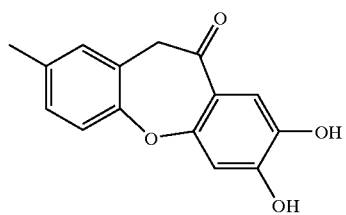

Compound 98

PRODUCTION EXAMPLE 100

Synthesis of 2-cyclohexyl-7,8-dihydroxy-10,11-dihydrodibenzo[b,f]oxepin-10-one (Compound 99)

In the same manner as in the first to the fifth stages of Production Example 98 except for the use of 2-bromo-4-cyclohexylphenol instead of 2-bromophenol in the third step of Production Example 98, the title Compound 99 represented by the following formula was prepared. The peaks of this Compound 99 in $^1$H-NMR (400 MHz, CDCl$_3$) were as follows.

δ1.24–1.40(m, 5H),
1.71–1.81(m, 5H),
2.6(m, 1H), 4.02(s, 2H),
6.90(s, 1H),
7.06–7.08(m, 2H),
7.15(d, 1H, J=8 Hz),
7.71(s, 1H).

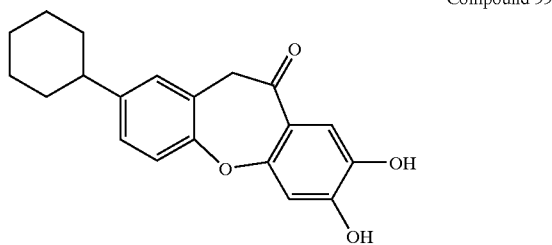

Compound 99

PRODUCTION EXAMPLE 101

Synthesis of 2-(1-butyl)-7,8-dimethoxy-10,11-dihydrodibenzo[b,f]oxepin-10-one (Compound 100)

In the same manner as in the first to the fifth stages of Production Example 98 except for the use of 2-bromo-4-(1-butyl)phenol instead of 2-bromophenol in the third step of Production Example 98, the title Compound 100 represented by the following formula was prepared. The peaks of this Compound 100 in $^1$H-NMR (400 MHz, CDCl$_3$) were as follows.

δ0.77(t, 3H, J=7 Hz),
1.25(m, 2H), 1.40(m, 2H),
2.36(m, 2H), 3.82(s, 2H),
6.70(s, 1H),
6.86(d, 1H, J=8 Hz),
6.92(s, 1H),
6.97(d, 1H, J=8 Hz),
7.32(s, 1H), 7.72(br, 2H).

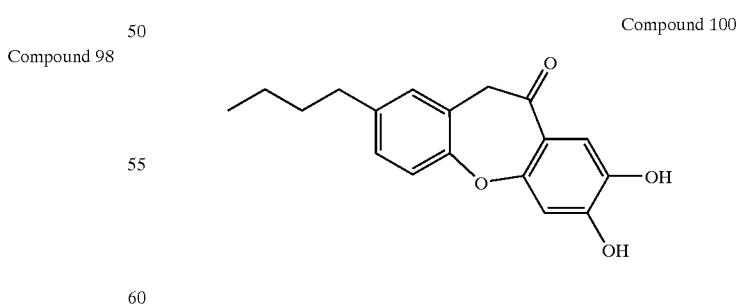

Compound 100

PRODUCTION EXAMPLE 100

Synthesis of 2-(tert-butyl)-7,8-dihydroxy-10,11-dihydrodibenzo[b,f]oxepin-10-one (Compound 101)

In the same manner as in the first to the fifth stages of Production Example 98 except for the use of 2-bromo-4-

(tert-butyl)phenol instead of 2-bromophenol in the third step of Production Example 98, the title Compound 101 represented by the following formula was prepared. The peaks of this Compound 101 in $^1$H-NMR (400 MHz, CDCl$_3$) were as follows.

δ1.16(s, 9H), 3.89(s, 2H), 6.76(1H, s), 7.02(d, 1H, J=8 Hz), 7.10–7.17(m, 2H), 7.39(1H, s).

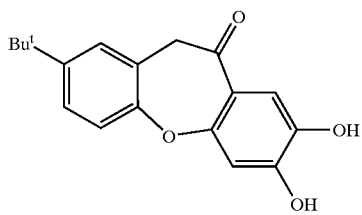

Compound 101

PRODUCTION EXAMPLE 103

Synthesis of 7,8-dihydroxy-1,3-dimethyl-10,11-dihydrodibenzo[b,f]oxepin-10-one (Compound 102)

In the same manner as in the first to the fifth stages of Production Example 98 except for the use of 2-bromo-3,5-dimethylphenol instead of 2-bromophenol in the third step of Production Example 98, the title Compound 102 represented by the following formula was prepared.

The peaks of this Compound 102 in $^1$H-NMR (400 MHz, CDCl$_3$) were as follows.

δ2.19(s 3H), 2.30(s, 3H), 3.96(s, 2H), 6.78(1H, s), 6.80(s, 1H), 6.85(s, 1H), 7.41(s, 1H), 7.46(br, 2H).

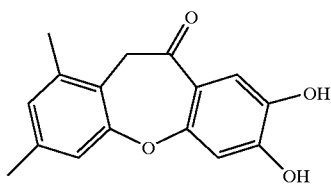

Compound 102

PRODUCTION EXAMPLE 104

Synthesis of 7,8-dihydroxy-2-phenyl-10,11-dihydrodibenzo[b,f]oxepin-10-one (Compound 103)

In the same manner as in the first to the fifth stages of Production Example 98 except for the use of 2-bromo-4-phenylphenol instead of 2-bromophenol in the third stage of Production Example 98, the title Compound 103 represented by the following formula was prepared.

The peaks of this Compound 103 in $^1$H-NMR (400 MHz, CDCl$_3$) were as follows.

δ4.00(s, 2H), 6.84(s, 1H), 7.2–7.5(m, 9H).

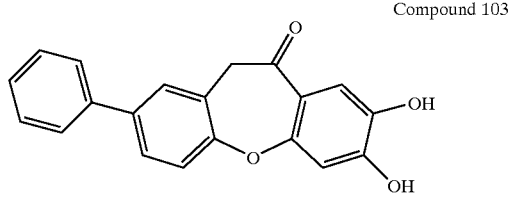

Compound 103

PRODUCTION EXAMPLE 105

Synthesis of 7,8-dihydroxy-10,11-dihydrodibenzo[b,f]thiepin-10-one (Compound 43)

First Stage

Synthesis of 2-(2-bromophenylthio)-4,5-dimethoxyacetophenone

To a solution of 2-bromothiophenol (380 mg) in N,N-dimethylformamide (2.5 ml) were added potassium carbonate (276 mg), copper acetate (540 mg) and 6-bromo-3,4-dimethoxyacetophenone (130 mg) and the mixture was stirred at 100° C. for four hours. The reaction mixture was diluted with ether, 5% solution hydroxide solution was added thereto and the mixture was stirred for five minutes. This was diluted with a mixture of ether and hexane and washed with 5% solution hydroxide solution, water and saturated sodium chloride solution successively. The organic layer was collected and dried over magnesium sulfate and the solvent was evaporated therefrom. The resulting residue was purified by a silica gel chromatography (hexane:ether 2:1) to give the title compound (250 mg, 56%) as yellow oil. The peaks of this compound in $^1$H-NMR (400 MHz, CDCl$_3$) were as follows.

δ2.63(s, 3H), 3.90(s, 3H), 3.94(s, 3H), 6.48(s, 1H), 7.18(dt, 1H, J=1.5, 7.0 Hz), 7.31(dt, 1H, J=1.8, 7.2 Hz), 7.66(dd, 1H, J=1.8, 8.1 Hz).

Second Stage

Synthesis of 7,8-dimethoxy-10,11-dihydrodibenzo[b,f]thiepin-10-one

To 2-(2-bromophenylthio)-4,5-dimethoxyacetophenone (Compound 20) (15 mg) were added liquid ammonia (1 ml) and potassium tert-butoxy (20 mg) in an argon atmosphere and the mixture were irradiated with light for 30 minutes. To the reaction mixture were added ether and ammonium chloride and the ether layer was collected. This was dried over magnesium sulfate and filtered with sodium sulfate. The solvent was evaporated to give the title compound (4.6 mg, 42%) as white crystals.

The peaks of this compound in $^1$H-NMR (400 MHz, CDCl$_3$) were as follows.

δ3.89(s, 3H), 3.96(s, 3H), 4.37(s, 2H), 7.04(s, 1H), 7.20(dt, 1H, J=7.3 Hz), 7.35(dt, 1H, J=7.7 Hz), 7.44(dd, 1H, J=7.3 Hz), 7.64(dd, 1H, J=7.3 Hz), 7.73(s, 1H).

Third Stage

Synthesis of 7,8-dihydroxy-10,11-dihydrodibenzo[b,f]thiepin-10-one (Compound 22)

In the same manner as in the fifth stages of Production Example 98 except for the use of 7,8-dimethoxy-10,11-dihydrodibenzo[b,f]thiepin-10-one instead of 7,8-dimethoxy-10,11-dihydrodibenzo[b,f]oxepin-10-one in the fifth stage of Production Example 98, the title compound (Compound 43) represented by the following formula was prepared. The peaks of this Compound 43 in $^1$H-NMR (400 MHz, CDCl$_3$) were as follows.

δ4.23(s 2H), 6.97(s, 1H),
7.2–7.5(m, 3H),
7.51(s, 1H),
7.6–7.7(m, 1H),
9.9(br, 2H).

PRODUCTION EXAMPLE 106

Synthesis of 7,8-dihydroxy-2-methyl-10,11-dihydrodibenzo[b,f]thiepin-10-one (Compound 104)

In the same manner as in the first to the fifth stages of Production Example 98 except for the use of 2-bromo-4-methylphenol instead of 2-bromophenol in the third step of Production Example 98, the title Compound 104 represented by the following formula was prepared. The peaks of this Compound 104 in $^1$H-NMR (400 MHz, CDCl$_3$—CD$_3$OD) were as follows.

δ2.25(s, 3H), 4.12(brs, 2H),
6.91(d, 1H, J=8 Hz),
6.96(s, 1H),
7.15(brs, 1H),
7.41(d, 1H, J=8 Hz),
7.51(s, 1H).

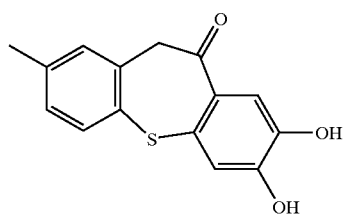

Compound 104

PRODUCTION EXAMPLE 107

Synthesis of 2-ethyl-7,8-dihydroxy-10,11-dihydrodibenzo[b,f]thiepin-10-one (Compound 105)

In the same manner as in the first to the fifth stages of Production Example 98 except for the use of 2-bromo-4-ethylphenol instead of 2-bromophenol in the third step of Production Example 98, the title Compound 105 represented by the following formula was prepared. The peaks of this Compound 105 in $^1$H-NMR (400 MHz, CDCl$_3$) were as follows.

δ1.20(t, 3H, J=7 Hz),
2.61(q 2H, J=7 Hz),
4.31(brs, 2H),
7.00(d, 1H, J=8 Hz),
7.08(s, 1H), 7.24(s, 1H),
7.51(d, 1H, J=8 Hz),
7.64(s, 1H).

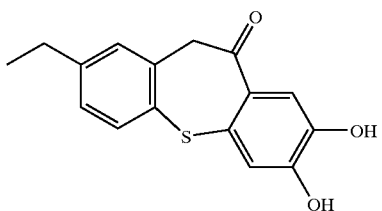

Compound 105

PRODUCTION EXAMPLE 108

Synthesis of 7,8-dihydroxy-2-(2-propyl)-10,11-dihydrodibenzo[b,f]thiepin-10-one (Compound 106)

In the same manner as in the first to the fifth stages of Production Example 98 except for the use of 2-bromo-4-(2-propyl)thiophenol instead of 2-bromophenol in the third step of Production Example 98, the title Compound 106 represented by the following formula was prepared. The peaks of this Compound 106 in $^1$H-NMR (400 MHz, CDCl$_3$) were as follows.

δ1.19(d, 6H, J=7 Hz),
2.89(sept, 1H, J=7 Hz),
4.30(brs, 2H),
7.02(dd, 1H, J=8, 2 Hz),
7.05(s, 1H),
7.24(d, 1H, J=2 Hz),
7.51(d, 1H, J=8 Hz),
7.61(s, 1H).

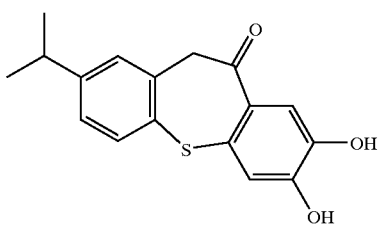

Compound 106

PRODUCTION EXAMPLE 109

Synthesis of 2-thiomethyl-9-hydroxy-7-methoxy-10,11-dihydrodibenzo[b,f]oxepin-10-one (Compound 107)

In the same manner as in the first to the fourth stages of Production Example 79 except for the use of 2-chloro-5-(methylthio)benzoic acid and 3,5-dimethoxyphenol instead of thiosalicylic acid and 5-chloro-1,3-dimethoxybenzene in Production Example 79, the title Compound 107 represented by the following formula was prepared. The melting point of this Compound 107 was 124–126° C.

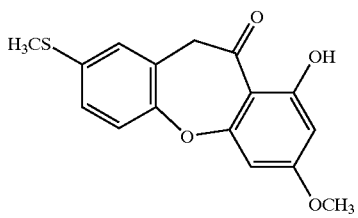

Compound 107

PRODUCTION EXAMPLE 110

Synthesis of 2-thiomethyl-7,9-dihydroxy-10,11-dihydrodibenzo[b,f]oxepin-10-one (Compound 108)

In the same manner as in the third stage of Production Example 8 except for the use of the Compound 107 prepared in the above Production Example 109, the title Compound 108 represented by the following formula was prepared. The melting point of this Compound 108 was 113–116° C.

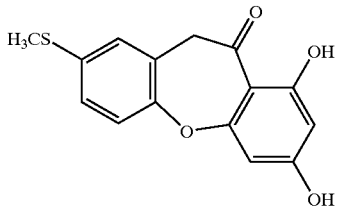

Compound 108

PRODUCTION EXAMPLE 111

Synthesis of 2-thiomethyl-7,9-dihydroxy-10,11-dihydrodibenzo[b,f]oxepin-10-one S-oxide (Compound 109)

To the Compound 108 (100 mg, F.W. 288.323, 0.327 mmol) prepared in the above Production Example 110 were added methanol (2 ml), water (2 ml) and periodic acid (76.6 mg, F. W. sodium 213.89, 0.36 mmol). The solution was stirred at room temperature for two hours and then ice water was added gradually thereto. This was extracted with ether followed by washing with water and saturated sodium chloride solution successively. The organic layer was dried over magnesium sulfate, the solvent was completely evaporated in vacuo and the residue was purified by a silica gel column chromatography (developing solvent; ethyl acetate:hexane=1:2). Further recrystallization from ethyl acetate-hexane gave 90 mg (F. W. 304.322, 86%) of the title Compound 109 represented by the following formula. The melting point of this Compound 109 was 233–236° C.

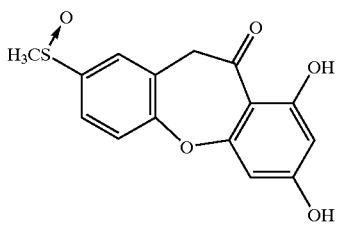

Compound 109

PRODUCTION EXAMPLE 112

Synthesis of 2-bromo-7,9-dihydroxy-10,11-dihydrodibenzo[b,f]oxepin-10-one (Compound 110)

First Stage

Synthesis of 2-bromo-7,9-dimethoxy-10,11-dihydrodibenzo[b,f]oxepin-10-one

In the same manner as in the first to the fourth stages of Production Example 79 except for the use of 2-chloro-5-bromobenzoic acid and 3,5-dimethoxyphenol instead of thiosalicylic acid and 5-chloro-1,3-dimethoxybenzene in Production Example 79, the title compound was prepared. The peaks of this compound in $^1$H-NMR (400 MHz, CDCl$_3$) were as follows.

3.84(3H, s, C$\underline{H}_3$),
3.88(3H, s, C$\underline{H}_3$),
3.96(2H, s, C$\underline{H}_2$),
6.27(1H, d, J=2.5 Hz, Ar—$\underline{H}$),
6.46(1H, d, J=2.5 Hz, Ar—$\underline{H}$),
7.09(1H, d, J=2.4 Hz, Ar—$\underline{H}$),
7.33(2H, dd, J=8.5, 2.4 Hz, Ar—$\underline{H}$),
7.42(1H, d, J=2.4 Hz, Ar—$\underline{H}$)

Second Stage

Synthesis of 2-bromo-7,9-dihydroxy-10,11-dihydrodibenzo[b,f]oxepin-10-one

In the same manner as in the third stage of Production Example 8 except for the use of 2-bromo-7,9-dimethoxy-10,11-dihydrodibenzo[b,f]oxepin-10-one in the third step of Production Example 8, the title Compound 110 represented by the following formula was prepared. The melting point of this compound was 113–116° C.

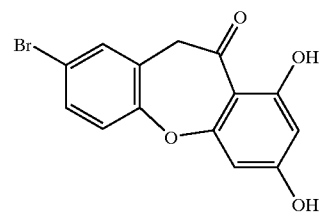

Compound 110

PRODUCTION EXAMPLE 113

Synthesis of 2-ethyl-9-hydroxy-7-methoxy-10,11-dihydrodibenzo[b,f]oxepin-10-one (Compound 111)

First Stage

Synthesis of 7,9-dimethoxy-2-trimethylsilylethynyl-10,11-dihydrodibenzo[b,f]oxepin-10-one 2-Bromo-7,9-dimethoxy-10,11-dihydrodibenzo[b,f]oxepin-10-one 500 mg (F. W. 349.18, 1.43 mmol) prepared in the first stage of Production Example 79, triphenylphosphine 75 mg (F. W. 262.29, 0.062 mmol), trisbenzylidene acetone dipalladium chloroform complex 74 mg (F. W. 1035.08, 0.015 mmol), diisopropylethylamine 575 μl (F. W. 98.22, d=0.742, 2.86 mmol), ethynyl trimethylsilane 350 μl (F. W. 98.22, d=0.742, 2.86 mmol) and copper iodide 27.5 mg (F. W. 190.44, 0.143 mmol) were dissolved in N-methyl-2-pyrrolidone (5 ml) and, after substituting with argon atmosphere, they were stirred with heating at 80° C. for one hour. The reaction mixture was diluted with ethyl acetate and washed with water and saturated sodium chloride solution. The organic layer was dried and concentrated and the resulting residue was purified by a silica gel column chromatography to give the title compound 420 mg (F. W. 367.419, 66%). The peaks of this compound in 1H-NMR (400 MHz, CDCl$_3$) were as follows.

1.21(3H, t, J=7.1 HZ, C$\underline{H}_3$), 2.60(2H, q, J=7.1 Hz, C$\underline{H}_2$), 3.82(3H, s, C$\underline{H}_3$), 3.85(3H, s, C$\underline{H}_3$), 3.95(2H, s, C$\underline{H}_2$), 6.24(1H, d, J=2.5 Hz, Ar—$\underline{H}$), 6.47(1H, d, J=2.5 Hz, Ar—$\underline{H}$), 7.05–7.25(3H, m, Ar—$\underline{H}$)

Second Stage

Synthesis of 2-ethyl-7,9-dimethoxy-10,11-dihydrodibenzo[b,f]oxepin-10-one 7,9-Dimethoxy-2-trimethylsilylethynyl-10,11-dihydrodibenzo[b,f]oxepin-10-one (220 mg) was dissolved in THF (11 ml) and, at 0° C., 1M-TABF-THF 0.35 ml (0.35 mmol) was added thereto followed by stirring at the same temperature for 15 minutes.

This was after-treated by a common method, then subjected to a reduction using Pd—C (12 mg) under hydrogen atmosphere and filtered and the filtrate was concentrated to give the title compound. The peaks of this compound in $^1$H-NMR (400 MHz, CDCl$_3$) were as follows.

1.21(3H, t, J=7.1 Hz, C$\underline{H}_3$), 2.60(2H, q, J=7.1 Hz, C$\underline{H}_2$), 3.82(3H, s, C$\underline{H}_3$), 3.85(3H, s, C$\underline{H}_3$), 3.95(2H, s, C$\underline{H}_2$), 6.24(1H, d, J=2.5 Hz, Ar—$\underline{H}$), 6.47(1H, d, J=2.5 Hz, Ar—$\underline{H}$), 7.05–7.25(3H, m, Ar—$\underline{H}$)

Third Stage

Synthesis of 2-ethyl-9-hydroxy-7-methoxy-10,11-dihydrodibenzo[b,f]oxepin-10-one In the same manner as in the third stage of Production Example 8 except for the use of 2-ethyl-7,9-dimethoxy-10,11-dihydrobenzo[b,f]oxepin-10-one prepared in the second stage, the title Compound 111 represented by the following formula was prepared. The peaks of this compound in $^1$H-NMR (400 MHz, CDCl$_3$) were as follows.

1.20(3H, t, J=7.1 Hz, C$\underline{H}_3$)

2.61(2H, q, J=7.1 Hz, C$\underline{H}_2$)

3.83(3H, s, C$\underline{H}_3$)

4.03(2H, s, C$\underline{H}_2$)

6.16(1H, d, J=2.5 Hz, Ar—$\underline{H}$)

6.38(1H, d, J=2.5 Hz, Ar—$\underline{H}$)

7.05–7.25(3H, m, Ar—$\underline{H}$)

13.05(1H, s, O$\underline{H}$)

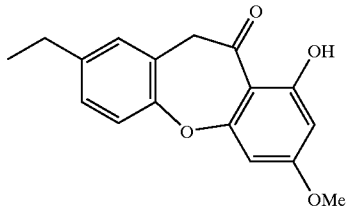

Compound 111

PRODUCTION EXAMPLE 114

Synthesis of 2-ethyl-7,9-dihydroxy-10,11-dihydrodibenzo[b,f]oxepin-10-one (Compound 112)

In the purification by a silica gel column chromatography in the third stage of the above Production Example 113, a compound having a higher polarity than the Compound 111 was purified to give the title Compound 112 represented by the following formula. The peaks of this compound in $^1$H-NMR (400 MHz, CDCl$_3$) were as follows.

1.20(3H, t, J=7.1 Hz, C$\underline{H}_3$)

2.61(2H, q, J=7.1 Hz, C$\underline{H}_2$)

4.03(2H, s, C$\underline{H}_2$)

6.16(1H, d, J=2.5 Hz, Ar—$\underline{H}$)

6.38(1H, d, J=2.5 Hz, Ar—$\underline{H}$)

6.55(1H, brs, O$\underline{H}$)

7.05–7.25(3H, m, Ar—$\underline{H}$)

13.05(1H, s, O$\underline{H}$)

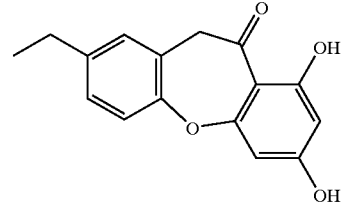

Compound 112

PRODUCTION EXAMPLE 115

Synthesis of 2-(1-phenyl-2-ethynyl)-7,9-dihydroxy-10,11-dihydrodibenzo[b,f]oxepin-10-one (Compound 113)

In the same manner as in the first to the third stages of Production Example 113 except for the use of phenylacetylene instead of ethynyl trimethylsilane in Production Example 113, the title Compound 113 represented by the following formula was synthesized. The peaks of this Compound 113 in $^1$H-NMR (400 MHz, CDCl$_3$) were as follows.

1.20(3H, t, J=7.1 Hz, C$\underline{H}_3$), 2.2(4H, m, C$\underline{H}_2$), 4.03(2H, s, C$\underline{H}_2$), 6.16(1H, d, J=2.5 Hz, Ar—$\underline{H}$), 6.38(1H, d, J=2.5 Hz, Ar—$\underline{H}$), 6.55(1H, brs, O$\underline{H}$), 7.0–7.7(8H, m, Ar—H),
13.02(1H, s, OH)

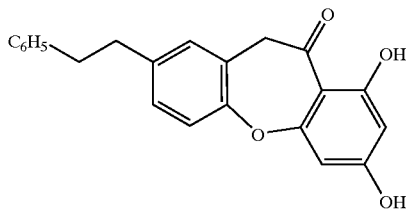

Compound 113

PRODUCTION EXAMPLE 116

Synthesis of 2-(3-hydroxy-1-propyl)-7,9-dihydroxy-10,11-dihydrodibenzo[b,f]oxepin-1-one (Compound 114)

The Compound 110 100 mg (F. W. 321.126, 0.31 mmol) prepared in Production Example 112, triphenylphosphine 16.2 mg (F. W. 262.29, 0.062 mmol), trisbenzylidene acetone dipalladium chloroform complex 16.2 mg (F. W. 1035.08, 0.015 mmol), diisopropylethylamine 125 μl (F. W. 98.22, d=0.742, 0.94 mmol), propargyl alcohol 76.3 μl (F. W. 73.14, d=0.963, 1.31 mmol), copper iodide 8.1 mg (F. W. 190.44, 0.043 mmol) and bistrimethylsilyl acetamide 0.5 ml (F. W. 203.43, d=0.836, 2.05 mmol) were dissolved in N-methylpyrrolidone (5 ml) and, after substituting with argon atmosphere, it was stirred at room temperature for two minutes and then stirred by heating at 80° C. for 16 hours. The reaction mixture was diluted with ethyl acetate and washed with water and saturated sodium chloride solution and the organic layer was dried and concentrated. The resulting residue was purified by a silica gel column chromatography to give the title Compound 114 represented by the following formula 33.8 mg (F. W. 296.278, 37%). The peaks of this Compound 114 in $^1$H-NMR (400 MHz, DMSO-d6) were as follows.

2.2(4H, m, CH$_2$),
4.01(2H, s, CH$_2$),
4.28(2H, s, CH$_2$),
5.55(1H, brs, OH),
6.08(1H, d, J=2.5 Hz, Ar—H),
6.36(1H, d, J=2.5 Hz, Ar—H),
7.0–7.7(3H, m, Ar—H),
12.96(1H, s, OH)

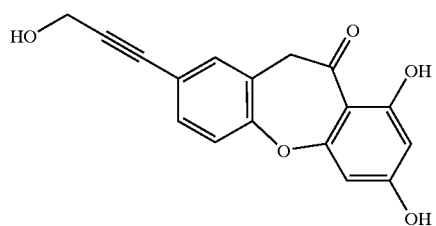

Compound 114

PRODUCTION EXAMPLE 117

Synthesis of 2-(4-hydroxy-1-butynyl)-7,9-dihydroxy-10,11-dihydrodibenzo[b,f]oxepin-10-one (Compound 115)

In the same manner as in Production Example 116 except for the use of 3-butyn-1-ol instead of propargyl alcohol in Production Example 116, the title Compound 115 represented by the following formula was prepared as yellow amorphous powder. The melting point of this Compound 115 was 174.1–176.1° C.

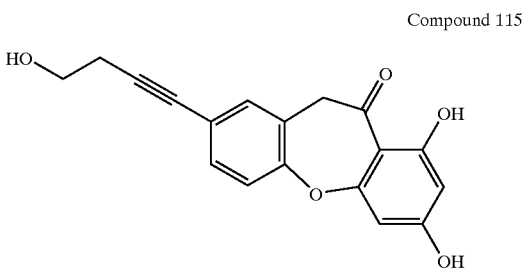

Compound 115

PRODUCTION EXAMPLE 118

Synthesis of 2-(5-hydroxy-1-pentynyl)-7,9-dihydroxy-10,11-dihydrodibenzo[b,f]oxepin-10-one (Compound 116)

In the same manner as in Production Example 116 except for the use of 4-pentyn-1-ol instead of propargyl alcohol in Production Example 116, the title Compound 116 represented by the following formula was prepared as pale yellow amorphous powder. The melting point of this Compound 116 was 174.9–176.6° C.

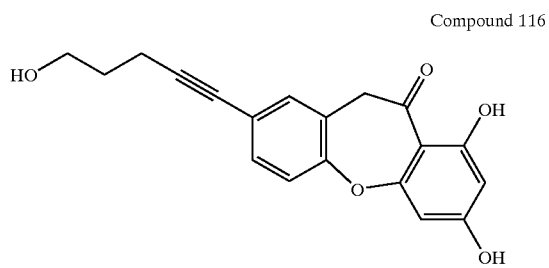

Compound 116

EXAMPLE 1

Dilating Action to Contraction of Tracheal Smooth Muscle

Each sample is tested by using two segment obtained from one animal; the trachea was removed from a guinea pig (Hartley, male, seven weeks age) and was made the segment, 6 mm in length. The segment was suspended in a Magnus tube containing a physiological salt solution of 37° C. with a flow of mixed gas consisting of 95% oxygen and 5% carbon dioxide gas. A base-line tension of 1 g was applied to the segment and, after tension of the sample became stable, the solution was exchanged with a solution containing 72.7 mM of potassium chloride to induce a contraction. When tension of the contraction by potassium chloride became stable, a compound of the formula (1) was added as a test substance to measure the change in the tension. The test substance was dissolved in dimethyl sulfoxide and added thereto. Incidentally, at the stage of addition, the final concentration of dimethyl sulfoxide was made not more than 0.3%. Changes in the tension was recorded on a recorder (R-64V, Rika Denki) after introducing to an amplifier for strain pressure (AP-621G, Nippon Koden Kogyo) via an FD pickup transducer (TB-611T, Nippon Koden Kogyo). Tension before addition of potassium chloride was set as 0 while that after addition of potassium chloride was set as 100 and the suppressing rate for contraction by potassium chloride after addition of the test substance was expressed by a relative percentage whereby the activity was determined according to the following criteria.
- −: no suppressing action of not less than 50% was achieved at 30 μM
- +: suppressing action of not less than 50% was achieved at 30 μM The result is shown in Table 1. The Compound No. in the table is the same as that in the Production Examples.

TABLE 1

| Compound No. | Activity |
|---|---|
| 2 | − |
| 7 | + |
| 8 | − |
| 9 | − |
| 11 | + |
| 12 | + |
| 13 | − |
| 14 | − |
| 15 | + |
| 16 | − |
| 19 | + |
| 20 | − |
| 23 | + |
| 24 | + |
| 27 | + |
| 28 | − |
| 29 | + |
| 30 | + |
| 34 | + |
| 35 | − |
| 36 | + |
| 37 | + |
| 38 | + |
| 39 | + |
| 40 | − |
| 44 | + |
| 47 | + |
| 49 | + |
| 63 | + |
| 70 | + |
| 71 | + |
| 77 | − |
| 80 | + |
| 81 | + |
| 82 | + |
| 84 | + |
| 85 | + |
| 86 | + |
| 89 | + |
| 90 | + |
| 91 | + |
| 92 | + |
| 94 | + |
| 95 | + |
| 96 | + |
| 97 | − |
| 104 | + |
| 106 | + |
| 108 | + |
| 109 | − |
| 110 | + |
| 111 | + |
| 112 | + |
| 113 | + |
| 114 | + |
| 115 | + |
| 116 | + |

Toxicity Test

Toxicity test was conducted only for the Compounds 11, 43 and 80 by means of a single oral administration to rats.
Animals used: three males
Dose: 2,000 mg/kg
The result was that no animal was dead and the minimum lethal dose was estimated to be not less than 2,000 mg/kg.

INDUSTRIAL APPLICABILITY

The present invention offers a tracheal smooth muscle relaxant useful as a pharmaceutical agent.

We claim:

1. A method for relaxing tracheal smooth muscle in an asthmatic subject comprising administering to said subject in need thereof an effective amount of a compound represented by formula (1):

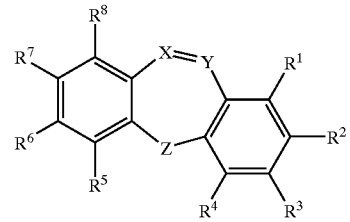

wherein
X and Y each is any member selected from the group consisting of $CH_2$, $CHW^1$, where $W^1$ is a halogen atom, a hydroxyl group or a lower alkoxy group and C=O when the bond between X and Y is a single bond while, when the bond between X and Y is a double bond, X and Y each is any member selected from the group consisting of CH and $COW^2$, where $W^2$ is a lower alkyl group or a lower alkylcarbonyl group;

Z is O; and $R^1$–$R^8$ each is selected from the group consisting of a hydrogen atom, $VR^9$, where V is O, S, S=O or $SO_2$; and $R^9$ is a hydrogen atom, a lower alkyl group, a hydroxy lower alkyl group, a lower acyl group, a trihalomethyl group or a carboxyl lower alkyl group; a hydroxy lower alkynyl group, a hydroxy lower alkenyl group, a halogen atom, a lower alkyl group, a trihalomethyl group, a trimethylsilylethynyl group, a nitro group, an amino group, an N-carbonyl lower alkyl group, a lower alkylphenyl group and a phenyl group or a pharmaceutically acceptable salt thereof.

2. The method as claimed in claim 1, wherein $R^3$ is hydroxy.

3. The compound as claimed in claim 1, wherein either $R^2$ or $R^3$ is hydroxy and the other is $OR^{10}$ where $R^{10}$ is selected from the group consisting of hydrogen, lower alkyl and lower alkyl carbonyl.

4. The method as claimed in claim 1, wherein either $R^1$ or $R^3$ is hydroxy and the other is $OR^{10}$ wherein $R^{10}$ is selected from the group consisting of hydrogen, lower alkyl and lower alkyl carbonyl.

5. The method as claimed in claim 1, wherein either $R^3$ or $R^4$ is hydroxy and the other is $OR^{10}$ wherein $R^{10}$ is selected from the group consisting of hydrogen, lower alkyl and lower alkyl carbonyl.

6. The method as claimed in claim 1, wherein the compound is

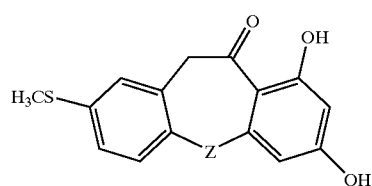

wherein:
Z is O.

* * * * *

UNITED STATES PATENT AND TRADEMARK OFFICE
CERTIFICATE OF CORRECTION

PATENT NO.    : 6,495,592 B1
DATED         : December 17, 2002
INVENTOR(S)   : Shinya Yamashita et al.

It is certified that error appears in the above-identified patent and that said Letters Patent is hereby corrected as shown below:

<u>Title page,</u>
Item [30], Foreign Application Priority Data, please change "007904" to -- 8-007904 --.

Signed and Sealed this

Eleventh Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,495,592 B1
DATED : December 17, 2002
INVENTOR(S) : Shinya Yamashita et al.

Page 1 of 1

It is certified that error appears in the above-identified patent and that said Letters Patent is hereby corrected as shown below:

Column 6,
Line 11, please change "

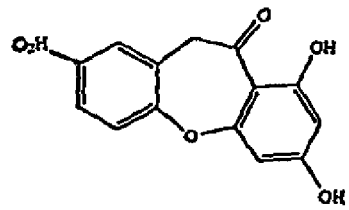

"

to --

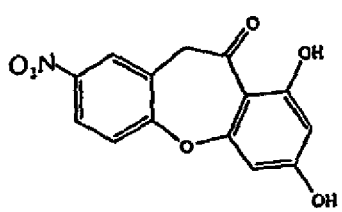

--.

Signed and Sealed this

Fifteenth Day of February, 2005

JON W. DUDAS
*Director of the United States Patent and Trademark Office*